US011337585B2

(12) United States Patent
Koda et al.

(10) Patent No.: US 11,337,585 B2
(45) Date of Patent: May 24, 2022

(54) CATHETER PLACEMENT DEVICE AND PLACEMENT SYSTEM

(71) Applicant: Coden Co., Ltd., Tokyo (JP)

(72) Inventors: Kojiro Koda, Tokyo (JP); Yoshiharu Koda, Tokyo (JP)

(73) Assignee: CODEN CO., LTD., Tokyo (JP)

( * ) Notice: Subject to any disclaimer, the term of this patent is extended or adjusted under 35 U.S.C. 154(b) by 296 days.

(21) Appl. No.: 16/293,786

(22) Filed: Mar. 6, 2019

(65) Prior Publication Data

US 2019/0192818 A1 Jun. 27, 2019

Related U.S. Application Data

(63) Continuation of application No. PCT/JP2018/034440, filed on Sep. 18, 2018.

(30) Foreign Application Priority Data

Nov. 2, 2017 (JP) .............................. JP2017-213267

(51) Int. Cl.
*A61B 1/00* (2006.01)
*A61B 1/04* (2006.01)
(Continued)

(52) U.S. Cl.
CPC ...... *A61B 1/00128* (2013.01); *A61B 1/00105* (2013.01); *A61B 1/00135* (2013.01);
(Continued)

(58) Field of Classification Search
CPC ............ A61M 25/0105; A61M 2250/00; A61J 15/00; A61J 15/0003; A61B 1/005;
(Continued)

(56) References Cited

U.S. PATENT DOCUMENTS 5,575,756 A * 11/1996 Karasawa .......... A61B 1/00068
600/121
5,989,183 A * 11/1999 Reisdorf ............ A61B 1/00142
600/156

(Continued)

FOREIGN PATENT DOCUMENTS

CN 1182374 A 5/1998
CN 1295826 A 5/2001
(Continued)

OTHER PUBLICATIONS

Office Action dated Jul. 7, 2020 issued in Indian Patent Application No. 202037014997.
(Continued)

*Primary Examiner* — Aaron B Fairchild
(74) *Attorney, Agent, or Firm* — Fox Rothschild LLP

(57) ABSTRACT

A placement device is provided for causing a catheter to be placed inside of a body. The placement device includes an insertion unit, a transmission unit and a supply member. The supply member includes a supply unit main body, and a projection. A through-hole is formed on the inner peripheral surface of the supply unit main body at a position closer to a distal end side of the supply portion main body than the projection, and the through-hole communicates with an inside of the supply unit main body at the distal end side of the supply unit main body.

17 Claims, 13 Drawing Sheets

(51) Int. Cl.
    *A61B 1/015*  (2006.01)
    *A61B 1/06*   (2006.01)
    *A61B 1/005*  (2006.01)
    *A61B 1/01*   (2006.01)
    *A61J 15/00*  (2006.01)
    *A61M 13/00*  (2006.01)
    *A61M 16/04*  (2006.01)
    *A61B 17/00*  (2006.01)
    *A61B 1/273*  (2006.01)
    *A61B 1/267*  (2006.01)
    *A61B 17/50*  (2006.01)

(52) U.S. Cl.
    CPC .............. *A61B 1/015* (2013.01); *A61B 1/042* (2013.01); *A61B 1/0684* (2013.01); *A61J 15/0003* (2013.01); *A61M 13/003* (2013.01); A61B 1/00045 (2013.01); A61B 1/0057 (2013.01); A61B 1/00078 (2013.01); A61B 1/01 (2013.01); A61B 1/0676 (2013.01); A61B 1/2676 (2013.01); A61B 1/2736 (2013.01); A61B 17/50 (2013.01); A61B 2017/00809 (2013.01); A61M 16/0415 (2014.02); A61M 16/0461 (2013.01)

(58) Field of Classification Search
    CPC ........... A61B 1/008; A61B 1/00; A61B 1/042; A61B 1/233; A61B 1/0669; A61B 1/015; A61B 1/00128; A61B 1/00045; A61B 1/0684; A61B 1/128; A61B 1/07; A61B 2017/306; A61B 17/50; A61B 2017/22035; A61B 2217/005; A61B 90/361; A61B 2017/242; A61B 1/2733; A61B 1/00135; A61B 1/051; A61B 1/01; A61B 1/00105; A61B 1/00078; A61B 1/0676
    See application file for complete search history.

(56)                References Cited

U.S. PATENT DOCUMENTS

| 6,458,323 B1    | 10/2002 | Boekstegers    |
| 2008/0177226 A1 | 7/2008  | Watanabe et al.|
| 2009/0318757 A1 | 12/2009 | Singh          |
| 2017/0065492 A1 | 3/2017  | Baba           |
| 2017/0143200 A1 | 5/2017  | Majima et al.  |

FOREIGN PATENT DOCUMENTS

| CN | 1950021 A     | 4/2007  |
| CN | 102743296 A   | 10/2012 |
| CN | 103006173 A   | 4/2013  |
| CN | 103071222 A   | 5/2013  |
| CN | 103622832 A   | 3/2014  |
| CN | 105662325 A   | 6/2016  |
| CN | 205994845 U   | 3/2017  |
| CN | 206548842 U   | 10/2017 |
| EP | 2928517 A1    | 10/2015 |
| JP | S59-122103 U  | 8/1984  |
| JP | H03-037030 A  | 2/1991  |
| JP | H03-056403 U  | 5/1991  |
| JP | H06-038902 U  | 5/1994  |
| JP | 2001-299687 A | 10/2001 |
| JP | 2004-008241 A | 1/2004  |
| JP | 2004-240202 A | 8/2004  |
| JP | 2010-117443 A | 5/2010  |
| JP | 4785831 B2    | 10/2011 |
| JP | 2012-523288 A | 10/2012 |
| JP | 2012-231897 A | 11/2012 |
| JP | 2013-180156 A | 9/2013  |
| JP | 5706879 B2    | 4/2015  |
| JP | 2016-150214 A | 8/2016  |
| JP | 6116783 B1    | 4/2017  |
| RU | 2445069 C2    | 3/2012  |
| WO | 2004/107951 A2| 12/2004 |
| WO | 2010/118256 A2| 10/2010 |
| WO | 2012/176720 A1| 12/2012 |
| WO | 2013/137372 A1| 9/2013  |
| WO | 2015/108957 A1| 7/2015  |
| WO | 2015/146652 A1| 10/2015 |
| WO | 2017/110757 A1| 6/2017  |

OTHER PUBLICATIONS

Extended European Search Report dated Mar. 17, 2020 issued in European Patent Application No. 18852707.1.
International Search Report dated Nov. 13, 2018 issued in PCT/JP2018/034440.
Office Action dated Dec. 5, 2017 issued in Japanese Patent Application No. 2017-213267.
Office Action dated Apr. 24, 2018 issued in Japanese Patent Application No. 2017-213267.
Notice of Allowance dated Jul. 24, 2018 issued in Japanese Patent Application No. 2017-213267.
Office Action dated Aug. 24, 2020 issued in Russian Patent Application No. 2020113186.
Chinese Notice of Allowance, with English translation of Search Report, dated Sep. 28, 2021 in related Chinese applicatrion No. 201880003397.6, 6 pages.
Huawen Li et al., "New development of visualization technology for double-lumen endotracheal intubation", Anhui Medical Journal, vol. 37, issue 2, Dec. 31, 2016, pp. 230-233.
Haolin Dong et al., "Current state of visualized endotracheal intubation technology", Medicine and Philosophy (B), vol. 37, issue 05, Dec. 31, 2016, pp. 64-66.
Office Action CN 201880003397.6 dated Apr. 19, 2021.

* cited by examiner

CATHETER PLACEMENT DEVICE AND PLACEMENT SYSTEM

CROSS REFERENCE TO RELATED APPLICATIONS

This application is a continuation application based on PCT/JP2018/034440, filed on Sep. 18, 2018 and claiming priority based on Japanese Patent Application No. 2017-213267, filed in Japan on Nov. 2, 2017. The contents of both the Japanese Patent Application and the PCT Application are incorporated herein by reference.

FIELD OF INVENTION

The present invention relates to a placement device and a placement system for causing a catheter to be placed inside of a body.

BACKGROUND

In the related art, a catheter has been used in order to treat a dysphagia patient who cannot swallow food or drink by oneself (for example, refer to Japanese Patent No. 5706879). After a digestive system surgery is performed, the catheter needs to be placed into a stomach (inside of a body) in order to clean the inside of the stomach or to lower internal pressure of the stomach or intestines.

In a current situation, users rely on their senses when inserting the catheter into which a guide wire is inserted into a nasal cavity. Since the wire is inserted into the catheter, the catheter is less likely to be compressed or is less likely to be bent in a longitudinal direction. Moreover, the catheter is inserted into the body through the nose of an examinee.

In a deep portion of the pharynx inside the body, the esophagus and the trachea are located close to each other. Since the trachea is used for breathing, the trachea is usually open. On the other hand, the esophagus is usually closed.

The inside of the body (pharynx) is not as easy to visually confirm. Accordingly, the catheter reaching the pharynx after being inserted through the nose may be incorrectly inserted into the trachea instead of the esophagus (by accidentally mistaking it for the esophagus) in some cases. Through an X-ray image or stomach sound obtained by a stethoscope, the user checks whether the catheter is correctly inserted into the esophagus. However, reliable measures to be taken upon incorrect insertion have not been established.

SUMMARY OF THE INVENTION (1) According to an aspect of the present invention, there is provided a placement device for causing a catheter to be placed inside of a body. The placement device includes an insertion unit which is flexible, and which is capable of being inserted into and removed from the catheter, the insertion unit being capable of observing an object located more distally than the insertion unit, a transmission unit which has a first connecting portion to be detachably connected to a proximal end portion of the insertion unit, and which transmits an image obtained by observation of the insertion unit or a signal obtained by converting the image, and a supply member into which the insertion unit is to be inserted so as to be drawable therefrom, and to which a proximal end portion of the catheter is to be detachably attached. The supply member includes a supply unit main body into which the insertion unit is to be inserted, and a projection which is formed of an elastic material over an entire periphery of the supply unit main body on an inner peripheral surface of the supply unit main body, and which contacts with the insertion unit and holds the insertion unit such that the insertion unit is capable of sliding. A through-hole is formed at a position closer to a distal end side of the supply portion main body than the projection on the inner peripheral surface of the supply unit main body, and the through-hole communicates with an inside of the supply unit main body at the distal end side of the supply unit main body.

According to an aspect of this invention, the distal end side is observed using the insertion unit. While the image obtained by the observation or the image converted again after the image is converted into the signal once is checked, for example, using a display unit, the catheter is guided and inserted into the body together with the insertion unit. After the catheter is guided to a proper position, the insertion unit of the placement device is removed from the catheter, and the catheter is caused to place. In the placement device, the insertion unit and the first connecting portion of the transmission unit are detachable from each other. Therefore, the insertion unit is detached from the first connecting portion. In this manner, a new insertion unit can be attached to the first connecting portion, or only the detached insertion unit can be cleaned without cleaning the transmission unit. Accordingly, the insertion unit can be easily maintained.

In addition, an outer surface of the supply member in the radial direction is covered by the proximal end portion of the catheter, and a fluid (a gas or a liquid) is supplied to the distal end side of the supply member. A portion is hermetically held between the outer peripheral surface of the insertion unit and the inner peripheral surface of the supply member. Accordingly, the fluid can be supplied to the distal end side through the portion between the outer peripheral surface of the insertion unit and the inner peripheral surface of the supply member. In this manner, the fluid flows between the inner peripheral surface of the catheter and the outer peripheral surface of the insertion unit. Accordingly, it is possible to prevent friction from occurring between them. As a result, for example, even in a case where a gap is very small between the catheter and the insertion unit, the insertion unit can be easily inserted into the catheter, or the insertion unit can be easily drawn out from the inside of the catheter.

In addition, in a state where the portion is hermetically held between the outer peripheral surface of the insertion unit and the inner peripheral surface of the supply member, the insertion unit can be inserted into the distal end side relative to the supply unit, or the insertion unit can be drawn out to the proximal end side relative to the supply unit.

(2) In the placement device according to (1) described above, a plurality of projections may be arranged on the inner peripheral surface of the supply unit main body.

(3) In the placement device according to (1) or (2) described above, the supply unit main body and the projection may be integrally formed of an elastic material.

(4) In the placement device according to any one of (1) to (3) described above, a locking portion may be provided at the proximal end portion of the catheter. An locked portion may be formed over the entire periphery of the supply unit main body on an outer peripheral surface of the supply unit main body and the locking portion may be locked to the locked portion. As the locking portion and the locked portion, it is conceivable to combine a projecting portion and a recessed portion with each other.

(5) In the placement device according to any one of (1) to (4) described above, the insertion unit may have a condenser lens which collects light from the distal end side of the insertion unit, and a light source which emits the light to the distal end side of the insertion unit, which generates heat, and which comes into contact with the condenser lens.

According to an aspect of this invention, the heat generated by the light source is transferred to the condenser lens so as to raise the temperature of the condenser lens. In this manner, it is possible to prevent dew condensation of the condenser lens which is caused by water vapor inside the body.

(6) In the placement device according to any one of (1) to (5) described above, an imaging element for acquiring the image may be located inside the transmission unit.

According to an aspect of this invention, the imaging element which is relatively expensive and not as easy to clean is not located inside the insertion unit. In this manner, the manufacturing cost of the insertion unit can be minimized, and the insertion unit can be easily cleaned.

(7) In the placement device according to any one of (1) to (6) described above, a second connecting portion having a second opening may be provided in the proximal end portion of the insertion unit. A sealing member which is detachable from the second opening and which hermetically covers the second opening may be connected to the insertion unit via an interlocking member.

According to an aspect of this invention, when the proximal end portion of the insertion unit is connected to the first connecting portion, the sealing member is detached from the second opening of the insertion unit. On the other hand, in a state where the second opening of the insertion unit is sealed using the sealing member, the insertion unit can be cleaned. Therefore, the insertion unit can be easily cleaned.

(8) In the placement device according to any one of (1) to (7) described above, the insertion unit may include an outer cover tube, an optical fiber inserted into the outer cover tube, and a lens or a transparent cover which covers the optical fiber from a proximal end side.

(9) In addition, according to an aspect of the present invention, there is provided a placement system including the placement device according to any one of (1) to (8) described above, and the catheter.

(10) In the placement system according to (9) described above, the catheter may include a tube main body that is formed in a tubular shape, and into which the insertion unit is inserted, and a first projection which projects inward in a radial direction from an inner peripheral surface of a distal end portion of the tube main body, and which is locked to a distal end surface of the insertion unit.

According to an aspect of this invention, when the catheter and the insertion unit are inserted into the body together, it is possible to prevent the insertion unit from being misaligned with the distal end side relative to the catheter.

(11) In the placement system according to (10) described above, the first projection may be provided in only a portion of the tube main body in a circumferential direction.

According to an aspect of this invention, the fluid can be easily supplied to the distal end side through the portion having no first projection in the circumferential direction between the inner peripheral surface of the tube main body and the outer peripheral surface of the insertion unit.

(12) In the placement system according to (10) or (11) described above, the catheter may include a second projection which projects inward in the radial direction from an inner peripheral surface of the tube main body.

According to an aspect of this invention, the outer peripheral surface of the insertion unit comes into contact with the distal end from which the second projection projects, thereby forming a gap between the inner peripheral surface of the tube main body and the outer peripheral surface of the insertion unit. Therefore, the fluid can easily flow to the distal end side through the gap.

(13) In the placement system according to (10) or (11) described above, the catheter may include a linear member which is formed of a more rigid material than the tube main body, and which is provided in the tube main body along an axis of the tube main body.

According to an aspect of this invention, while the catheter maintains bendability in a direction perpendicular to an axis of the tubular main body, the catheter can be less likely to be deformed in an axial direction of the tube main body.

(14) In the placement system according to (13) described above, a portion of the linear member may project inward in the radial direction from an inner peripheral surface of the tube main body, and a remaining portion of the linear member may be buried into the tube main body.

According to an aspect of this invention, the outer peripheral surface of the insertion unit comes into contact with the distal end from which the linear member projects, thereby forming a gap between the inner peripheral surface of the tube main body and the outer peripheral surface of the insertion unit. Therefore, the fluid can easily flow to the distal end side through the gap. In addition, since the linear member projects, a contact surface decreases between the distal end portion from which the linear member projects and the outer peripheral surface of the insertion unit. Accordingly, it is possible to reduce frictional resistance occurring therebetween. In this case, the linear member also serves as a member for forming the gap between the inner peripheral surface of the tube main body and the outer peripheral surface of the insertion unit. Therefore, it is possible to minimize the number of components for configuring the catheter.

(15) In addition, according to an aspect of the present invention, there is provided a placement system including the placement device according to any one of (1) to (8) described above, and the catheter. The catheter has a tube main body formed in a tubular shape, and a guide tube into which the insertion unit is inserted, the guide tube being attached to an outer peripheral surface of the tube main body or being located inside the tube main body.

According to an aspect of this invention, in a state where the insertion unit is inserted into the guide tube, drugs can be administered, or ascites can be discarded using the tube main body.

(16) The placement system according to any one of (9) to (15) described above may further include a fluid supply unit that supplies a fluid to the through-hole.

(17) In the placement system according to (16) described above, the fluid supply unit may include a pressure feeding tube whose distal end portion is to be inserted into the through-hole.

DETAILED DESCRIPTION OF THE INVENTION

The present invention provides a placement device and a placement system for causing a catheter to be placed inside of a body.

First Embodiment

Hereinafter, a first embodiment of a placement system according to the present invention will be described with reference to FIGS. 1 to 10.

Figure 1:
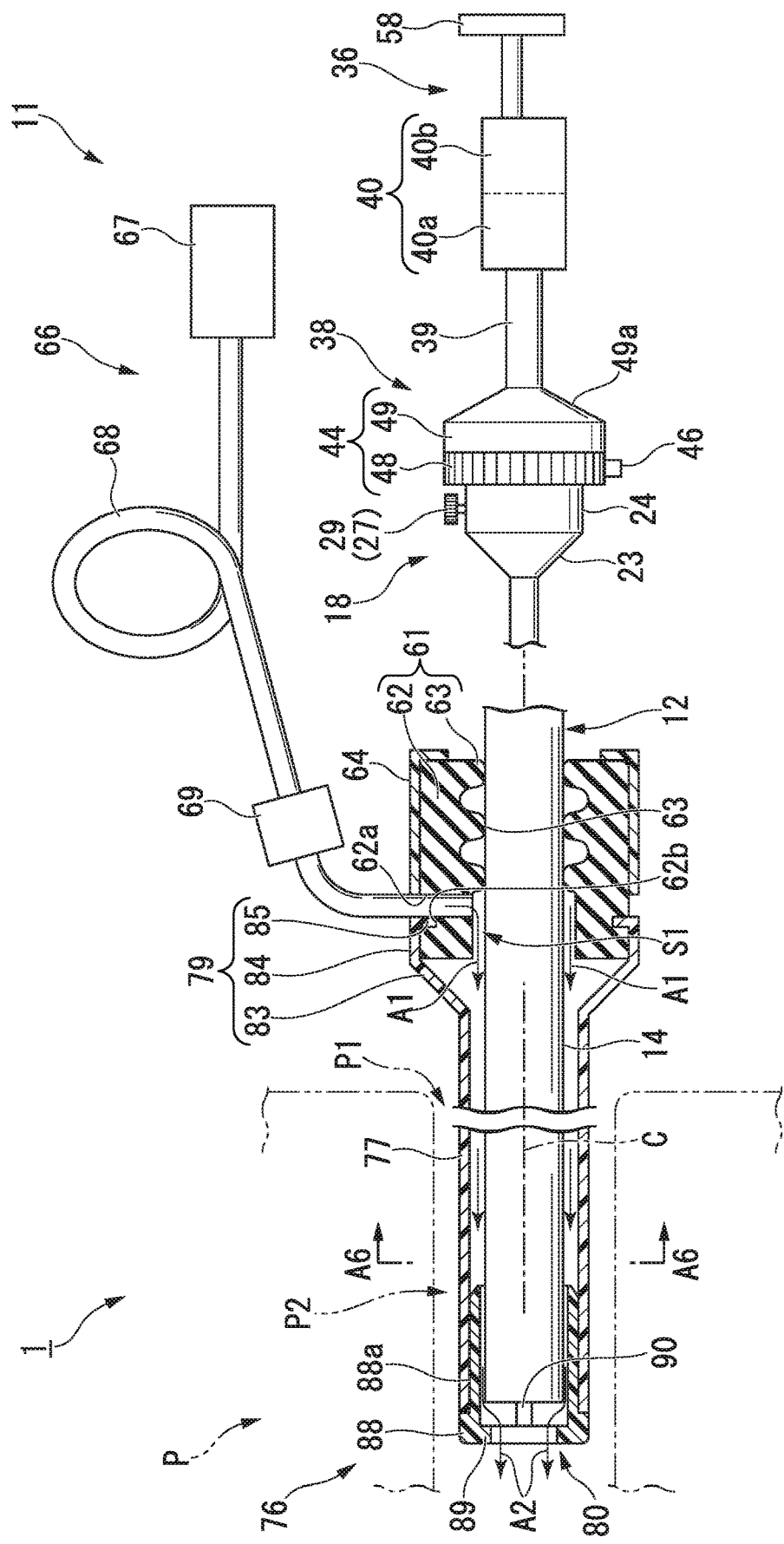
FIG. 1 is a partially broken side view showing a placement system according to a first embodiment of the present invention.

As shown in FIG. 1, a placement system 1 according to the present embodiment includes a placement device 11 according to the present embodiment and a catheter 76. The placement device 11 causes the catheter 76 to place the inside of a body. The inside of the body described herein is not limited to the inside of a human body, but may also be the inside of an animal such as a dog or a cat.

The placement device 11 includes an insertion unit (lead cable) 12, a transmission unit 36, a display unit 58, a supply member 61, and a gas supply unit 66 (fluid supply unit).

Figure 2:
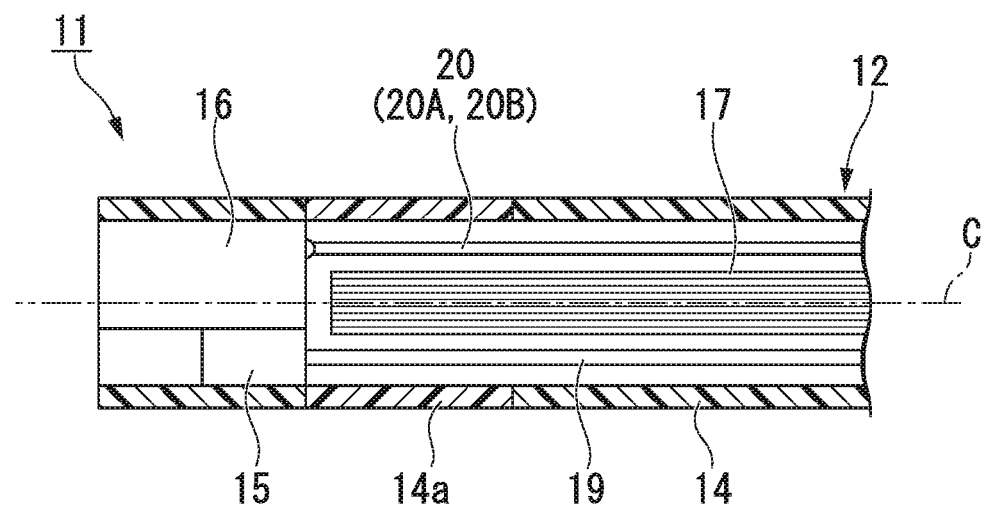
FIG. 2 is a sectional view when a distal end portion in a lead cable of an placement device of the placement system is viewed in a side view.
Figure 3:
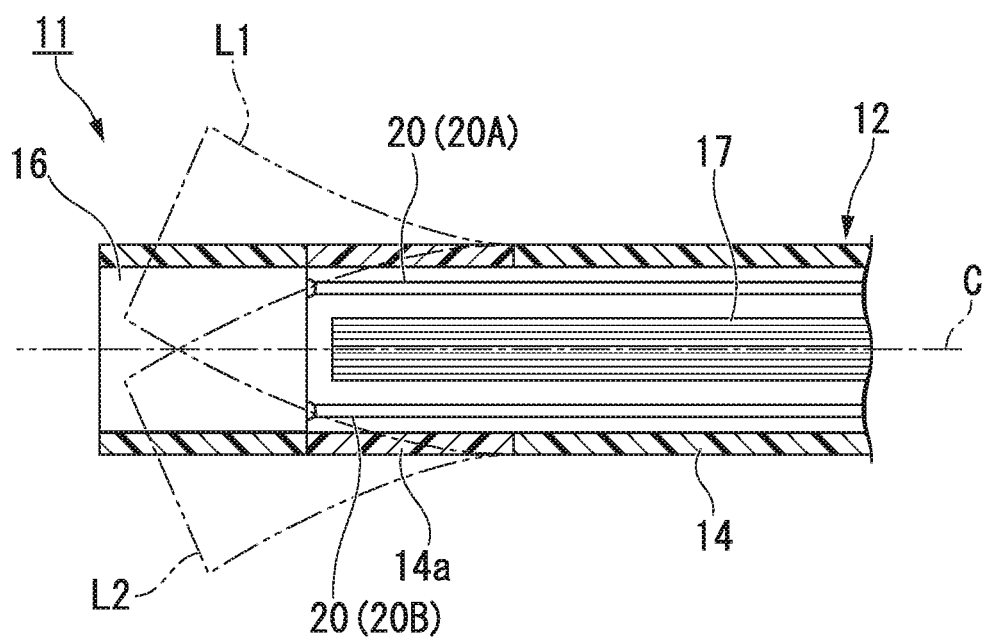
FIG. 3 is a sectional view when the distal end portion in the lead cable is viewed in a side view.
Figure 4:
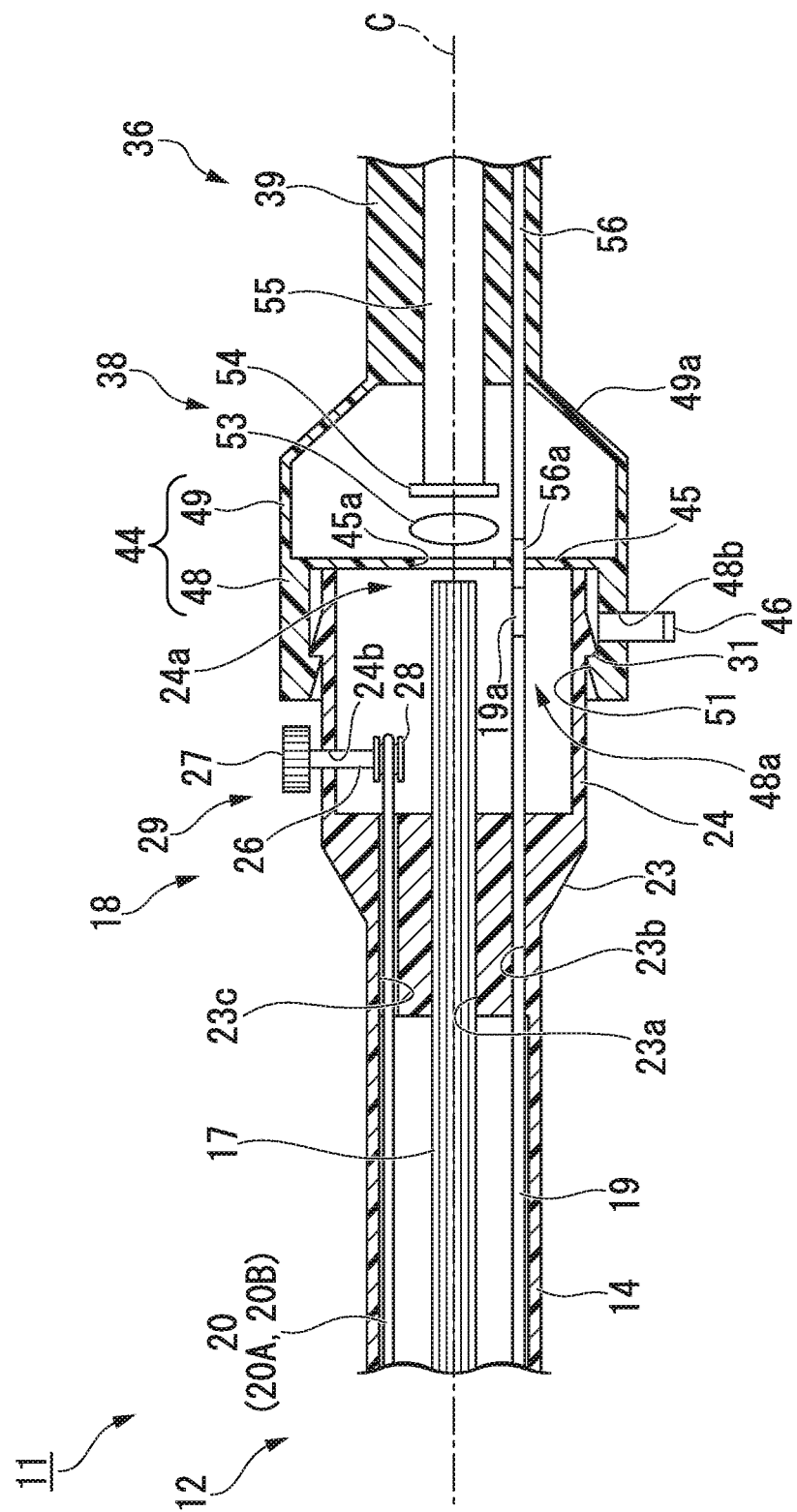
FIG. 4 is a sectional view when a state where a first connector of the lead cable and a second connector of a display unit are connected to each other is viewed in a side view.

As shown in FIGS. 2 to 4, the lead cable 12 is formed to be elongated. The lead cable 12 has an outer cover tube 14, a light emitting diode (LED, a light source) 15, a condenser lens 16, an optical fiber 17, and a first connector (second connecting portion) 18.

The outer cover tube 14 is formed of a resin or a flexible coil material in a circular tube shape. It is preferable that a flexible portion 14a that is less rigid than other portions in the outer cover tube 14 be formed in a proximal side portion located a predetermined length from a distal end in the outer cover tube 14. For example, the flexible portion 14a can be formed by changing a physical property of the resin or a wire diameter of the coil to be different from that of other portions. The flexible portion 14a is formed in a cylindrical shape.

If predetermined power is supplied to the LED 15, the LED 15 emits light to a distal end side. In this case, the LED 15 generates a certain amount of heat. A distal end portion of a first power line 19 for supplying the power to the LED 15 is connected to a proximal end portion of the LED 15. The first power line 19 extends toward a proximal end side inside the outer cover tube 14. FIG. 2 is a longitudinal sectional view of the lead cable 12 in a first radial direction thereof.

The condenser lens 16 causes the light emitted from the distal end side toward the proximal end side of the lead cable 12 to be collected on a distal end surface of the optical fiber 17. The condenser lens 16 may be formed from one lens, or may be formed from a plurality of lenses. For example, the one or plurality of lenses configuring the condenser lens 16 are accommodated in a housing (not shown). The housing is formed in a cylindrical shape. The housing is fixed to an inner peripheral surface of a distal end side portion from the flexible portion 14a in the outer cover tube 14 by using an adhesive.

The LED 15 is in contact with a side surface of the housing. The LED 15 is fixed to the housing using an adhesive. In the description herein, the statement that A (for example, the LED 15) comes into contact with B (for example, the condenser lens 16) includes not only the case in which A directly comes into contact with B but also the case in which A indirectly comes into contact with B via other members.

A distal end portion of a pair of operation wires 20 is fixed to a proximal end portion of the housing. The pair of operation wires 20 extend toward the proximal end side inside the outer cover tube 14. In a plan view shown in FIG. 3 (in other words, when the lead cable 12 is viewed in a second direction perpendicular to the first direction in the radial direction), the pair of operation wires 20 are located across an axis C of the outer cover tube 14. The axis C and the axis C of the tube main body 77 of the catheter 76 (to be described later) coincide with each other.

If an operation wire 20A which is one of the pair of operation wires 20 is pulled toward the proximal end side, the flexible portion 14a is deformed. Therefore, as shown by a two-dot chain line L1 in FIG. 3, a distal end portion of the outer cover tube 14 is bent in a first orientation relative to the axis C. On the other hand, if an operation wire 20B which is the other of the pair of operation wires 20 is pulled toward the proximal end side, the flexible portion 14a is deformed. Therefore, as shown by a two-dot chain line L2, the distal end portion of the outer cover tube 14 is bent in a second orientation relative to the axis C.

By operating the pair of operation wires 20 in this way, the distal end portion of the lead cable 12 can be bent in the first orientation and the second orientation.

As shown in FIG. 4, the proximal end portions of the pair of operation wires 20 are connected to each other. The pair of operation wires 20 are formed in a U shape in a plan view.

As shown in FIGS. 2 and 3, the optical fiber 17 is located so as to face the condenser lens 16 on the proximal end side from the condenser lens 16. The optical fiber 17 extends toward the proximal end side inside the outer cover tube 14. The optical fiber 17 is supported by a support member (not shown) relative to the outer cover tube 14. The optical fiber 17 guides the light collected from the condenser lens 16 to the optical fiber 17 to the proximal end side through the inside of the optical fiber 17.

As shown in FIG. 4, the first connector 18 is located on the proximal end side from the outer cover tube 14, that is, in the proximal end portion of the lead cable 12. The first connector 18 has an interlocking portion 23 and a first connecting member 24.

The interlocking portion 23 is formed in a columnar shape. An outer diameter of a distal end portion of the interlocking portion 23 is equal regardless of a position in a direction of the axis C. The outer diameter of a proximal end portion of the interlocking portion 23 gradually increases toward the proximal end side. The outer diameter of the distal end portion of the interlocking portion 23 and the outer diameter of the outer cover tube 14 are equal to each other. The interlocking portion 23 is connected to the proximal end portion of the outer cover tube 14 coaxially with the outer cover tube 14.

Through-holes 23a, 23b, and 23c into which the optical fiber 17, the first power line 19, and the operation wire 20 are inserted are each formed in the interlocking portion 23. The through-holes 23a, 23b, and 23c extend in the direction of the axis C.

The first connecting member 24 is formed in a cylindrical shape, and is located more proximally than the interlocking portion 23. An opening (second opening) 24a is formed in the proximal end portion of the first connecting member 24.

The outer diameter of the first connecting member 24 and the outer diameter of the proximal end portion of the interlocking portion 23 are equal to each other. The first connecting member 24 is connected to the proximal end portion of the interlocking portion 23 coaxially with the interlocking portion 23.

The first connecting member 24 is not limited to a cylindrical shape, and may have a rectangular tube shape. Similarly, the interlocking portion 23 is not limited to a columnar shape, and may have a cylindrical shape.

The first connecting member 24 has a through-hole 24b penetrating the first connecting member 24 in the radial direction. The through-hole 24b is formed in an intermediate portion in the first connecting member 24 in the direction of the axis C.

A rotary shaft 26 is inserted into the through-hole 24b. An operation dial 27 is fixed to an end portion located outside the first connecting member 24 in the rotary shaft 26. A pulley 28 is fixed to an end portion located inside the first connecting member 24 in the rotary shaft 26. In a state where the pair of operation wires 20 are stretched, mutually connected portions in the pair of operation wires 20 are wound around the pulley 28. The rotary shaft 26, the operation dial 27, and the pulley 28 configure a bending controller 29.

If the operation dial 27 is rotated in the first orientation around the axis of the rotary shaft 26, the operation wire 20A is pulled toward the proximal end side, and the distal end portion of the outer cover tube 14 is bent in the first orientation relative to the axis C. On the other hand, if the operation dial 27 is rotated in the second orientation around the axis of the rotary shaft 26, the operation wire 20B is pulled toward the proximal end side, and the distal end portion of the outer cover tube 14 is bent in the second orientation relative to the axis C.

In this way, the operation dial 27 of the bending controller 29 is rotated, thereby enabling the distal end portion of the lead cable 12 to be bent in the first orientation and the second orientation.

A first claw 31 is provided on the proximal end side from the through-hole 24b on the outer peripheral surface in the first connecting member 24. The first claw 31 projects outward in the radial direction of the first connecting member 24. The first claw 31 may be provided over the entire periphery of the first connecting member 24, or a plurality of first claws 31 may be provided at an interval in the circumferential direction of the first connecting member 24.

The proximal end portion of the optical fiber 17 and the proximal end portion of the first power line 19 extend to the vicinity of the proximal end portion of the first connecting member 24. A first connecting terminal 19a such as a contact is attached to the proximal end portion of the first power line 19.

For example, the interlocking portion 23, the first connecting member 24, and the first claw 31 are integrally formed of an elastic material such as a resin.

The lead cable 12 configured in this way is flexible, and has the LED 15, the condenser lens 16, and the optical fiber 17. Accordingly, the lead cable 12 can observe an object located more distally than a distal end of the lead cable 12. As shown in FIG. 1, the lead cable 12 is inserted into the catheter 76.

The transmission unit 36 transmits the image obtained by observation of the lead cable 12. The transmission unit 36 has a second connector (first connecting portion) 38, a connecting cable 39, and a control unit 40.

As shown in FIG. 4, the second connector 38 has a second connecting member 44, a positioning plate 45, and an operation button 46. The second connecting member 44 has a first cylindrical body 48 and a second cylindrical body 49.

The first cylindrical body 48 is formed in a cylindrical shape. An opening (first opening) 48a is formed in the distal end portion of the first cylindrical body 48. The inner diameter of the first cylindrical body 48 is larger than the outer diameter of the first connecting member 24 of the first connector 18. The first cylindrical body 48 covers the proximal end portion of the first connecting member 24 from the outside in the radial direction. A second claw 51 is provided on the inner peripheral surface of the distal end portion of the first cylindrical body 48. The second claw 51 projects inward in the radial direction of the first cylindrical body 48. The second claw 51 engages with the first claw 31 of the first connector 18 from the distal end side of the first claw 31. In this way, the second connector 38 of the transmission unit 36 is connected to the first connector 18 provided in the proximal end portion of the lead cable 12.

A through-hole 48b penetrating the first cylindrical body 48 in the radial direction is formed in the proximal end side portion from the second claw 51 in the first cylindrical body 48. The through-hole 48b is located outward in the radial direction of the first claw 31 of the first connector 18.

The operation button 46 is inserted into the through-hole 48b. In a state shown in FIG. 4, the operation button 46 is located outward in the radial direction of the first claw 31. In this case, the first connecting member 24 is in a natural state where the first connecting member 24 does not receive an external force applied by the operation button 46.

The positioning plate 45 is located so as to close the opening on the proximal end side of the first cylindrical body 48. The positioning plate 45 is located so that a thickness direction of the positioning plate 45 extends in the direction of the axis C. An opening 45a penetrating the positioning plate 45 in the direction of the axis C is formed at a position facing the proximal end portion of the optical fiber 17 in the positioning plate 45.

The proximal end portion of the first connecting member 24 of the first connector 18 is in contact with the distal end side surface of the positioning plate 45.

The second cylindrical body 49 is formed in a cylindrical shape. The second cylindrical body 49 is located on the proximal end side from the first cylindrical body 48. The outer diameter of the distal end portion of the second cylindrical body 49 and the outer diameter of the first cylindrical body 48 are equal to each other. The second cylindrical body 49 is coaxially connected to the first cylindrical body 48. The proximal end portion of the second cylindrical body 49 has a reduced diameter portion 49a in which the outer diameter and the inner diameter gradually decrease toward the proximal end side.

The second cylindrical body 49 and the first cylindrical body 48 are not limited to the cylindrical shape, and may have a rectangular tube shape.

A lens 53 is located at a position facing the opening 45a of the positioning plate 45 inside the second cylindrical body 49. An imaging element 54 such as a complementary MOS (CMOS) or a charge coupled device (CCD) is located at a position on the proximal end side from the lens 53, which faces the lens 53. The imaging element 54 is located inside the second cylindrical body 49 of the transmission unit 36.

The lens 53 and the imaging element 54 are supported by a support member (not shown) relative to the second cylindrical body 49.

The transmission unit 36 has a function of adjusting focus of the lens 53 by changing a distance in the direction of the axis C between the lens 53 and the imaging element 54.

The light guided through the inside of the optical fiber 17 to the proximal end side passes through the inside of the opening 45a of the positioning plate 45, and is incident on the lens 53, thereby causing the lens 53 to form an image on a light receiving surface of the imaging element 54.

The imaging element 54 acquires the light image formed on the light receiving surface, and converts the image into a signal. A distal end portion of a signal line 55 is connected to the imaging element 54. The imaging element 54 transmits a signal to the proximal end side through the inside of the signal line 55.

The distal end portion of the second power line 56 is located inside the second cylindrical body 49. A second connecting terminal 56a such as a contact is attached to the distal end portion of the second power line 56. The second connecting terminal 56a penetrates the positioning plate 45 to the distal end side, and is exposed to the distal end side from the positioning plate 45. The second connecting terminal 56a is detachably connected to the first connecting terminal 19a of the first power line 19 in the direction of the axis C.

The distal end portion of the connecting cable 39 is coaxially connected to the proximal end portion of the reduced diameter portion 49a of the second cylindrical body 49 in the second connector 38. The signal line 55 and the second power line 56 extend toward the proximal end side inside the connecting cable 39.

Figure 5:
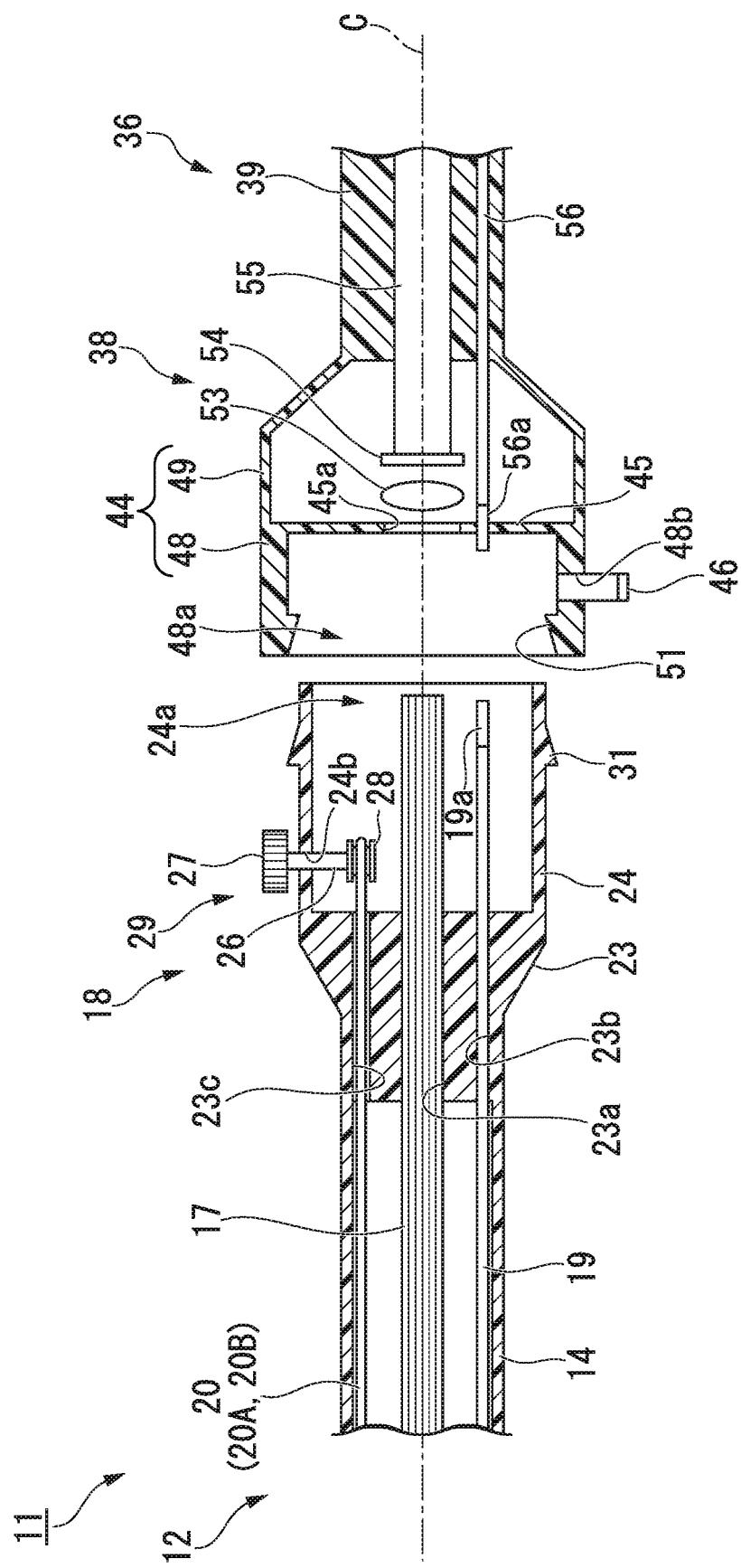
FIG. 5 is a sectional view when a state where the first connector of the lead cable is detached from the second connector of the display is viewed in a side view.

In a state where the transmission unit 36 is connected to the lead cable 12 in this way, the operation button 46 is pressed toward the axis C. Then, the first connecting member 24 is elastically deformed toward the axis C via the first claw 31. As shown in FIG. 5, the first claw 31 and the second claw 51 disengage from each other in the direction of the axis C. Then, the lead cable 12 is detached from the transmission unit 36. In this case, a connection between the second connecting terminal 56a of the second power line 56 and the first connecting terminal 19a of the first power line 19 is released. The first connecting member 24 is restored and deformed toward a side opposite to the axis C.

On the other hand, if the first connector 18 is pressed to the proximal end side relative to the second connector 38, the first claw 31 comes into contact with the second claw 51, and the first connecting member 24 is elastically deformed toward the axis C. When the proximal end portion of the first connecting member 24 comes into contact with the positioning plate 45, the first connecting member 24 is restored and deformed toward the side opposite to the axis C, and the first claw 31 and the second claw 51 engage with each other in the direction of the axis C. In this way, in a state where the opening 48a and the opening 24a communicate with each other, the first connector 18 and the second connector 38 are connected to each other. In this manner, the second connector 38 is connected to the first connector 18.

In this way, the first connector 18 of the lead cable 12 is attachable to and detachable from the second connector 38 of the transmission unit 36.

According to the present embodiment, the first connector 18 of the lead cable 12 and the second connector 38 of the transmission unit 36 are attachable to and detachable from each other by means of claw fitting between the first claw 31 and the second claw 51. However, a mechanism for detachably attaching the first connector and the second connector to each other is not limited to the claw fitting, and screw fitting may be used.

The bending controller 29 which bends the distal end portion of the lead cable 12 is provided in the first connector 18. However, the bending controller 29 may be provided in the second connector 38.

As shown in FIG. 1, the control unit 40 has an image processing unit 40a and a power supply unit 40b. The control unit 40 is provided on the connecting cable 39.

The image processing unit 40a appropriately converts the signal transmitted through the inside of the signal line 55 so that the display unit 58 can display the signal. The proximal end portion of the signal line 55 is connected to the display unit 58 together with the proximal end portion of the connecting cable 39.

The proximal end portion of the second power line 56 is connected to the power supply unit 40b. The power supply unit 40b supplies the power to the image processing unit 40a and the second power line 56.

The control unit 40 and the second connector 38 may be configured to be integrated with each other.

For example, the display unit 58 is a liquid crystal type display panel. The display unit 58 displays the observed image on the distal end side of the lead cable 12 based on the signal converted by the image processing unit 40a. The display unit 58 receives the signal transmitted from the image processing unit 40a, converts the signal, and displays the image obtained by the observation of the lead cable 12.

The supply member 61 has a supply unit main body 62 and a projection 63. The supply unit main body 62 is formed in a cylindrical shape. The inner diameter of the supply unit main body 62 is larger than the outer diameter of the outer cover tube 14 of the lead cable 12.

A plurality of (three in the present embodiment) projections 63 are located on the inner peripheral surface of the proximal end portion of the supply unit main body 62. The plurality of projections 63 project inward in the radial direction of the supply unit main body 62 from the inner peripheral surface of the proximal end portion of the supply unit main body 62. The respective projections 63 are formed over the entire periphery of the supply unit main body 62. The inner diameter of the projection 63 is equal to the outer diameter of the outer cover tube 14 of the lead cable 12, or is smaller than the outer diameter of the outer cover tube 14.

It is preferable that the outer peripheral surface of the proximal end portion of the supply unit main body 62 be covered with a cover 64.

A gap S1 is formed between the inner peripheral surface of the distal end portion of the supply unit main body 62 and the outer peripheral surface of the outer cover tube 14. A through-hole 62a penetrating the supply unit main body 62 in the radial direction is formed in a portion between the proximal end portion and the distal end portion in the supply unit main body 62. The through-hole 62a communicates with the gap S1.

A groove 62b (locked portion) is formed at a position on the distal end side from the through-hole 62a within the outer peripheral surface of the supply unit main body 62. The groove 62b is formed over the entire periphery of the supply unit main body 62.

The supply unit main body 62 and the plurality of projections 63 are integrally formed of an elastic material such as rubber or a resin, or a satisfactorily slidable material.

The lead cable 12 is inserted into the supply unit main body 62. The distal end portion in a projecting direction of the plurality of projections 63 is in contact with the outer peripheral surface of the outer cover tube 14 of the lead cable 12. The plurality of projections 63 are contacted to the outer cover tube 14. A portion between the plurality of projections 63 and the outer cover tube 14 is held in an airtight manner (hermetically). The lead cable 12 inserted into the supply unit main body 62 is slidable in the direction of the axis C relative to the plurality of projections 63 while the plurality of projections 63 are contacted to the outer cover tube 14 in the airtight manner.

If a gas (a fluid) is supplied into the through-hole 62a from the outside of the supply member 61, as shown by an arrow A1, the gas is supplied to the distal end side of the supply member 61 through the inside of the through-hole 62a and the inside of the gap S1.

The gas is not limited to air. Carbon dioxide gas, sterilized or disinfected air, and sterilized or disinfected carbon dioxide gas can be used. Furthermore, a liquid may be adopted instead of the gas.

The gas supply unit 66 has an air blower 67, a pressure feeding tube 68, and a tube locking portion 69. The air blower 67 fetches the gas from the outside, and raises the pressure of the gas to a predetermined pressure. The air blower 67 supplies the gas whose pressure is raised to the pressure feeding tube 68.

The proximal end portion of the pressure feeding tube 68 is connected to the air blower 67. The distal end portion of the pressure feeding tube 68 is connected to the through-hole 62a of the supply member 61. The tube locking portion 69 is used when the pressure feeding tube 68 is locked to a support member.

Figure 6:
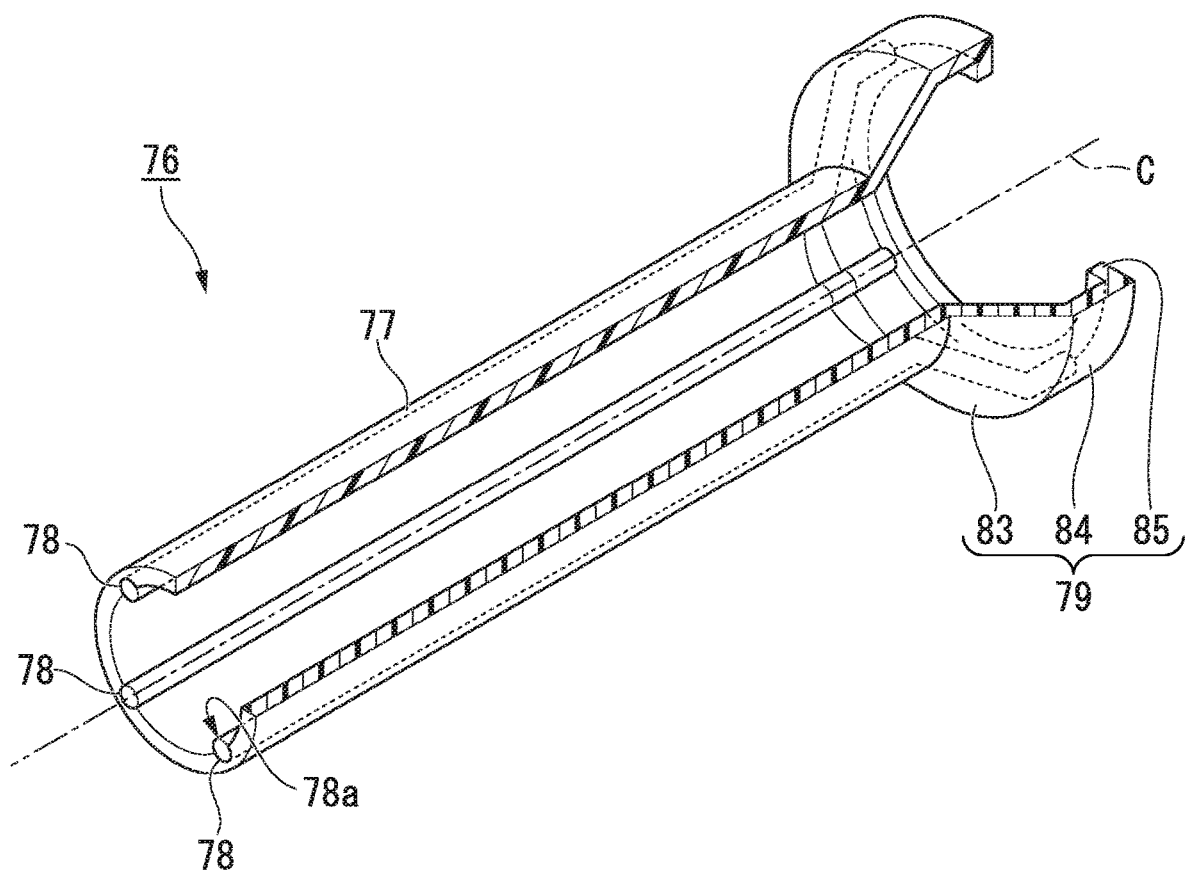
FIG. 6 is a partially broken perspective view showing a catheter of the placement system.

As shown in FIGS. 1 and 6, the catheter 76 includes a tube main body 77, a linear member 78, a proximal end side locking member 79, and a distal end side locking member 80. In FIG. 6, the distal end side locking member 80 is not shown.

The tube main body 77 is formed in a tubular shape using a resin such as silicon. The inner diameter of the tube main body 77 is larger than the outer diameter of the lead cable 12 of the placement device 11. The lead cable 12 is inserted into and removed from the tube main body 77.

The linear member 78 is formed of a material such as a resin which is more rigid than the material for forming the tube main body 77 (for example, silicon) and which is less likely to stretch or shrink in a pulling direction. The linear member 78 is provided in the tube main body 77 along the axis C of the tube main body 77.

When the lead cable 12 is drawn out from the catheter 76, the catheter 76 adheres to the lead cable 12, the catheter 76 is pulled, and the catheter 76 tries to move to the proximal end side of the lead cable 12 together with the lead cable 12. However, in this case, due to the linear member 78 which is less likely to shrink in a longitudinal direction (direction of the axis C) inside the catheter 76, a drawing force is likely to be directly transmitted to the lead cable 12. Therefore, the lead cable 12 can be drawn out without moving the catheter 76.

Figure 7:
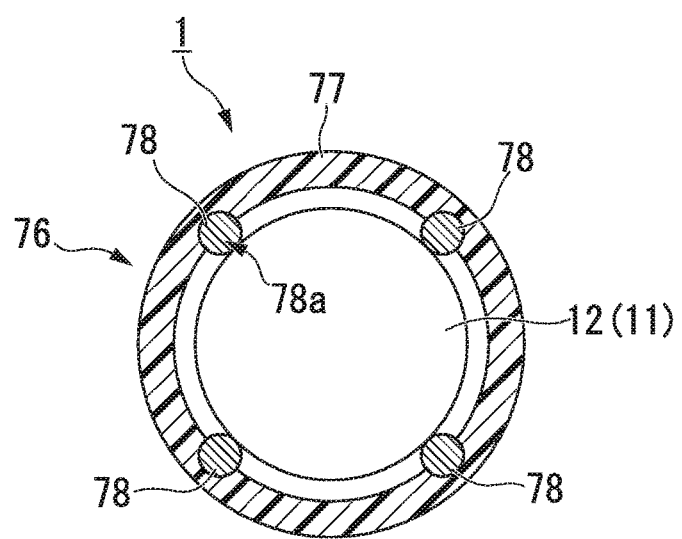
FIG. 7 is a sectional view taken along line A6-A6 in FIG. 1.

As shown in FIGS. 6 and 7, in this example, a portion of the linear member 78 projects inward in the radial direction from the inner peripheral surface of the tube main body 77. The remaining portion of the linear member 78 is buried into the tube main body 77. A portion projecting from the inner peripheral surface of the tube main body 77 in the linear member 78 configures a second projection 78a. In the tube main body 77, a plurality of (four in the present embodiment) linear members 78 are located at an interval around the axis C.

According to the present embodiment, the second projection 78a is formed over the entire length of the tube main body 77 in the direction of the axis C. However, the second projection 78a may be formed in a portion where the distal end side of the locking member 80 is not located, specifically, in an intermediate portion of the tube main body 77 in the direction of the axis C or in the proximal end portion.

As shown in FIGS. 1 and 6, the proximal end side locking member 79 has an interlocking portion 83, a large diameter portion 84, and a locking portion 85.

The interlocking portion 83 is formed in an annular shape. As the interlocking portion 83 faces toward the proximal end side, the outer diameter and the inner diameter gradually increase. The distal end portion of the interlocking portion 83 is coaxially connected to the proximal end portion of the tube main body 77. The large diameter portion 84 is formed in a cylindrical shape projecting over the entire periphery from the proximal end portion toward the proximal end side of the interlocking portion 83. The inner diameter of the large diameter portion 84 and the outer diameter of the supply unit main body 62 of the supply member 61 are equal to each other. The locking portion 85 is formed in an annular shape, and is inserted into the groove 62b of the supply member 61. In this manner, the locking portion 85 is locked to the groove 62b. In the shown example, the locking portion 85 is a projecting portion, and the groove 62b serving as a locked portion is a recessed portion. However, a relationship between the projecting portion and the recessed portion may be reversed. That is, for example, the recessed portion (for example, a groove or a through-hole) serving as the locking portion 85 may be provided in the proximal end side locking member 79, and the projecting portion serving as the locked portion may be provided in the supply member 61.

The tube main body 77 and the proximal end side locking member 79 can be formed simultaneously and integrally by means of insert molding in which the linear member 78 is located in a mold.

The catheter may be attached to the supply member 61 by covering the outer peripheral surface of the supply unit main body 62 of the supply member 61 with the proximal end portion of the tube main body 77. In this case, the proximal end portion of the tube main body 77 functions as the proximal end side locking member having no projecting and recessed shape in the radial direction.

Figure 8:
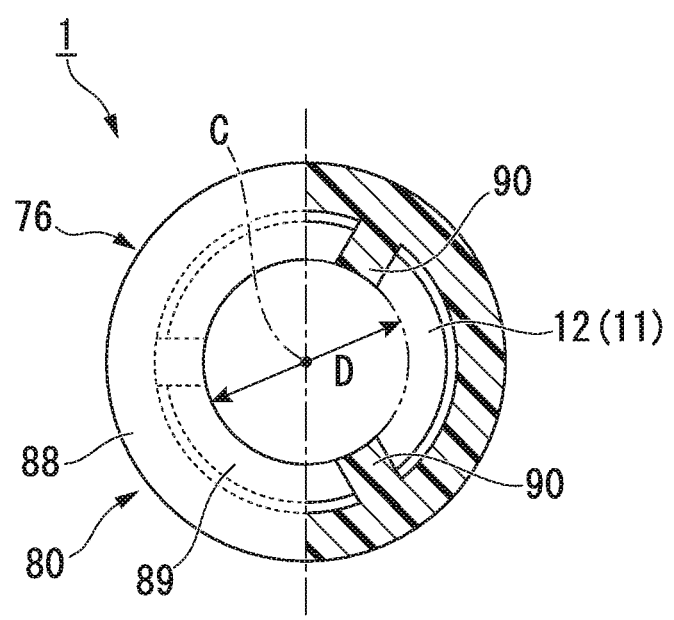
FIG. 8 is a half-sectional view when the placement system is viewed in a front view.

As shown in FIGS. 1 and 8, the distal end side locking member 80 has a cylindrical body 88, a distal end side projection 89, and a proximal end side projection (first projection) 90.

The cylindrical body 88 is formed in a cylindrical shape. In a portion other than the distal end portion on the outer peripheral surface of the cylindrical body 88, a stepped portion 88*a* is formed by reducing the outer diameter of the cylindrical body 88. The outer diameter of the stepped portion 88*a* and the inner diameter of the tube main body 77 are equal to each other. The inner diameter of the cylindrical body 88 is larger than the outer diameter of the outer cover tube 14 of the lead cable 12. The stepped portion 88*a* of the cylindrical body 88 is inserted into the distal end portion of the tube main body 77, and is attached to the tube main body 77.

The distal end side projection 89 is formed in an annular shape, and projects inward in the radial direction from the inner peripheral surface of the distal end portion of the tube main body 77.

The proximal end side projection 90 is located parallel to the distal end side projection 89 on the proximal end side from the distal end side projection 89. The proximal end side projection 90 projects inward in the radial direction of the tube main body 77 from the inner peripheral surface of the distal end portion of the tube main body 77. A plurality of (three in the present embodiment) proximal end side projections 90 are located with an interval therebetween around the axis C. That is, the proximal end side projection 90 is provided only in a portion of the tube main body 77 in the circumferential direction.

As shown in FIG. 8, for example, the inner diameter of the distal end side projection 89 and a diameter D of a virtual circle defined by an edge portion on the axis C side of the plurality of proximal end side projections 90 are equal to each other. The diameter D is smaller than the outer diameter of the outer cover tube 14 of the lead cable 12. Therefore, when the lead cable 12 of the placement device 11 is inserted into the catheter 76, the plurality of proximal end side projections 90 are locked to the distal end surface of the lead cable 12 from the distal end side of the lead cable 12.

The catheter 76 may be configured to include only the tube main body 77.

Next, a placing method of the catheter 76 using the placement system 1 configured as described above will be described.

First, a user moves the supply member 61 to the distal end side relative to the lead cable 12, and positions the supply member 61 in the distal end portion of the lead cable 12. The pressure feeding tube 68 of the gas supply unit 66 is connected to the through-hole 62*a* of the supply member 61. The air blower 67 is activated so as to supply the gas into the through-hole 62*a* through the pressure feeding tube 68. The gas is supplied to the distal end side of the supply member 61 from between the inner peripheral surface of the distal end portion of the supply unit main body 62 and the outer peripheral surface of the outer cover tube 14.

Next, the locking portion 85 of the proximal end side locking member 79 of the catheter 76 is inserted into the groove 62*b* of the supply member 61. In this manner, the catheter 76 is locked to the supply member 61. Thereafter, as described above, while the gas is supplied to the supply member 61 from the air blower 67, the lead cable 12 is moved to the distal end side relative to the supply member 61, and the lead cable 12 is inserted into the catheter 76. In this case, the gas is supplied to the distal end side by gas supply (supply member 61). Accordingly, the gas flows between the inner peripheral surface of the catheter 76 and the outer peripheral surface of the lead cable 12. As a result, it is possible to prevent friction therebetween. Therefore, even if a gap is small between the catheter 76 and the lead cable 12, the lead cable 12 is easily inserted into the catheter 76. Thereafter, the distal end surface of the lead cable 12 is locked to the plurality of proximal end side projections 90 of the catheter 76.

When the lead cable 12 is inserted into the catheter 76, the supply member 61 may be removed once from the lead cable 12. In this case, in a state where the supply member 61 is detached from the lead cable 12, the locking portion 85 of the catheter 76 can be fitted into the groove 62*b* of the supply member 61. Thereafter, the supply member 61 is loaded in the distal end of the lead cable 12. If the supply member 61 is moved to the proximal end side of the lead cable 12 while the gas is supplied from the supply member 61, the whole catheter 76 can be easily mounted on the lead cable 12.

Figure 9:
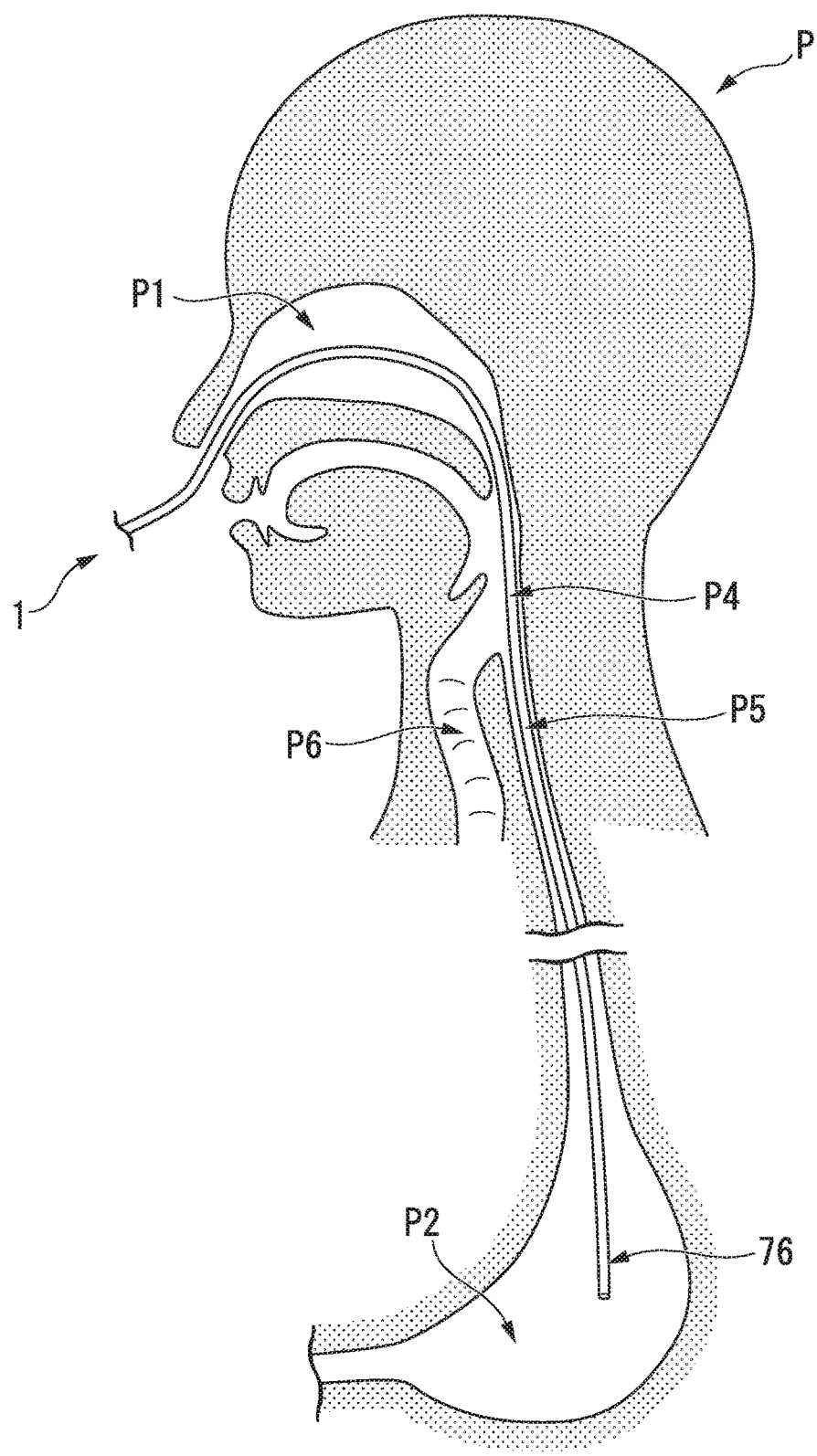
FIG. 9 is a view for describing a placing method of the catheter using the placement system.

The transmission unit 36 is connected to the lead cable 12 in advance. If the placement device 11 is activated, the power is supplied from the power supply unit 40*b* to the image processing unit 40*a* and the second power line 56. The power supplied to the second power line 56 is supplied to the LED 15 via the first power line 19. The LED 15 emits the light to the distal end side. While the user observes the image obtained by the observation of the lead cable 12 on the display unit 58 via the transmission unit 36, as shown in FIGS. 1 and 9, the catheter 76 having the inserted lead cable 12 is inserted through the nasal cavity P1 (opening of a human body) of a patient P.

The plurality of proximal end side projections 90 are locked to the distal end surface of the lead cable 12. Therefore, if the lead cable 12 is inserted into the body, a force of inserting the lead cable 12 is also transmitted to the tube main body 77 via the proximal end side projection 90. In this manner, not only the lead cable 12 but also the catheter 76 can be inserted into the body.

If the gas is continuously supplied while the catheter 76 is inserted into the body, the gas supplied to the distal end side of the supply member 61 as shown by an arrow A1 in FIG. 1 flows outward from the catheter 76 through the opening inside the distal end side projection 89 as shown by an arrow A2. The gas flows between the inner surface of the nasal cavity P1 and the outer peripheral surface of the catheter 76. In this manner, it is possible to prevent a body fluid of the patient P from adhering to and contaminating the catheter 76 and the lead cable 12. In addition, the gas flows into the stomach P2 of the patient P shown in FIG. 9. Accordingly, the stomach P2 (object) bulges, and thus the inside of the stomach P2 is easily observed.

When the distal end of the catheter 76 is located in the pharynx P4, if it is observed using the display unit 58 that the distal end of the catheter 76 is about to be inserted into the trachea P6 instead of the esophagus P5, the following countermeasures are taken.

That is, the proximal end portion of the lead cable 12 is rotated around the axis C so as to change an orientation of the distal end portion of the catheter 76. The catheter 76 tends to be bent in some cases. In this case, if the orientation of the catheter 76 is changed, an orientation for inserting the catheter 76 is changed. In addition, the catheter 76 is affected by gravity. Accordingly, the lead cable 12 (catheter 76) may be rotated so that the orientation for inserting the catheter 76 is changed downward.

In addition, a orientation of the patient P is changed so that the distal end of the catheter 76 is easily inserted into the esophagus P5. The catheter 76 is affected by gravity.

Accordingly, the orientation of the patient P is changed so that an orientation in which the catheter 76 needs to be inserted is changed downward.

If the catheter 76 is located at a desired position, while the gas is continuously supplied by the gas supply unit 66, the lead cable 12 is drawn out from the catheter 76. The gas flows between the inner peripheral surface of the catheter 76 and the outer peripheral surface of the lead cable 12. Therefore, the friction therebetween is prevented, and thus the lead cable 12 is easily drawn out from the catheter 76. The supply member 61 is detached from the catheter 76, and the catheter 76 is caused to place the inside of the body of the patient P.

Through the above-described steps, the placing of the catheter 76 is completed.

The placing catheter 76 is used in order to supply nutrients, drugs, or cleaning agents into organs such as the stomach P2 through the catheter 76, for example. That is, according to the present embodiment, a space (passage) into which the lead cable 12 is inserted and a flow passage for circulating a liquid such as the nutrients to be supplied into the body of the patient P from the outside are the same space (lumen).

Subsequently, in the case of using the placement device 11 so that the catheter 76 is caused to place another patient, the following steps are performed.

The used lead cable 12 is detached from the placement device 11. A new lead cable 12 is attached to the second connector 38, and the new lead cable 12 is used so that the catheter 76 is caused to place another patient as described above.

As described above, according to the placement device 11 of the present embodiment, the distal end side is observed using the lead cable 12. The image obtained by the observation is converted into the signal once by the imaging element 54. Thereafter, while the converted image is checked again using the display unit 58, the catheter 76 having the inserted lead cable 12 (insertion unit member) is inserted into the body. After the catheter 76 is guided to a proper position, the lead cable 12 of the placement device 11 is drawn from the catheter 76, and the catheter 76 is caused to place the body. The lead cable 12 and the second connector 38 of the transmission unit 36 are attachable to and detachable from the placement device 11. Therefore, the new lead cable 12 can be attached to the second connector 38 after detaching the insertion unit from the second connector 38 and only the detached lead cable 12 can be cleaned without cleaning the transmission unit 36. Accordingly, the lead cable 12 can be easily maintained, and the cost required for maintenance of the placement device 11 can be prevented.

The lead cable 12 has the condenser lens 16 and the LED 15. Therefore, the heat generated by the LED 15 is transferred to the condenser lens 16 so as to raise the temperature of the condenser lens 16. In this manner, it is possible to prevent dew condensation of the condenser lens 16 which is caused by water vapor inside the body.

The placement device 11 includes the supply member 61. The outer surface of the supply member 61 in the radial direction is covered with the proximal end portion of the catheter 76, and the gas is supplied to the distal end side of the supply member 61. In this case, a gap is held in an airtight manner (hermetically) between the outer peripheral surface of the lead cable 12 and the inner peripheral surface of the supply member 61. Therefore, the gas can be preferentially supplied to the distal end side instead of the proximal end side through the gap between the outer peripheral surface of the lead cable 12 and the inner peripheral surface of the catheter 76. In this manner, the gas flows between the inner peripheral surface of the catheter 76 and the outer peripheral surface of the lead cable 12. Accordingly, it is possible to prevent the friction therebetween. As a result, the lead cable 12 can be easily inserted into the catheter 76, or the lead cable 12 can be easily drawn out from the inside of the catheter 76.

In addition, in a state where the gap is held in the airtight manner between the outer peripheral surface of the lead cable 12 and the inner peripheral surface of the supply member 61, the lead cable 12 can be inserted into the distal end side relative to the supply member 61, or the lead cable 12 can be drawn to the proximal end side relative to the supply member 61. When the lead cable 12 is inserted into the catheter 76, for example, the supply member 61 is moved to the distal end side of the lead cable 12. In a state where the proximal end portion of the catheter 76 is locked to the supply member 61, the supply member 61 can be moved to the proximal end side of the lead cable 12 while the gas is supplied to the supply member 61. Alternatively, in a state where the supply member 61 is detached from the lead cable 12, the proximal end portion of the catheter 76 is locked to the supply member 61. Thereafter, while the gas is supplied to the supply member 61, the lead cable 12 is inserted into the supply member 61. In this manner, the supply member 61 can also be moved to the proximal end side of the lead cable 12.

The supply member 61 moves relative to the lead cable 12. Accordingly, the placement device 11 according to the present embodiment is applicable to various catheters having mutually different lengths.

The imaging element 54 is located inside the transmission unit 36. The imaging element 54 which is relatively expensive and not as easy to clean is not located inside the lead cable 12. In this manner, the manufacturing cost of the lead cable 12 can be minimized, and the lead cable 12 can be easily cleaned.

In addition, according to the placement system 1 of the present embodiment, the proximal end side projection 90 is locked to the distal end surface of the lead cable 12. Therefore, when the catheter 76 and the lead cable 12 are inserted into the body together, it is possible to prevent the lead cable 12 from being misaligned with the distal end side relative to the catheter 76.

The proximal end side projection 90 is provided only in a portion of the tube main body 77 in the circumferential direction. In this manner, the gas can be easily supplied to the distal end side through a portion having no proximal end side projection 90 in the circumferential direction, between the inner peripheral surface of the tube main body 77 and the outer peripheral surface of the lead cable 12.

The catheter 76 includes the second projection 78a. Therefore, the outer peripheral surface of the lead cable 12 comes into contact with the distal end from which the second projection 78a projects. In this manner, a gap is formed between the inner peripheral surface of the tube main body 77 and the outer peripheral surface of the lead cable 12. Therefore, the gas can easily flow to the distal end side through the gap.

The catheter 76 includes the linear member 78. Therefore, while the catheter 76 maintains bendability in a direction perpendicular to the axis C, the catheter 76 can be less likely to be deformed in the direction of the axis C. In this manner, when the lead cable 12 is drawn out from the catheter 76 placing the inside of the body, it is possible to prevent the placing catheter 76 from being inadvertently moved.

A portion of the linear member 78 projects inward in the radial direction from the inner peripheral surface of the tube main body 77, and the remaining portion of the linear member 78 is buried into the tube main body 77. The outer peripheral surface of the lead cable 12 comes into contact with the distal end from which the linear member 78 projects, thereby forming a gap between the inner peripheral surface of the tube main body 77 and the outer peripheral surface of the lead cable 12. Therefore, the gas can easily flow to the distal end side through the gap. The linear member 78 also serves as a member for forming the gap between the inner peripheral surface of the tube main body 77 and the outer peripheral surface of the lead cable 12. Accordingly, it is possible to minimize the number of components configuring the catheter 76.

Figure 10:
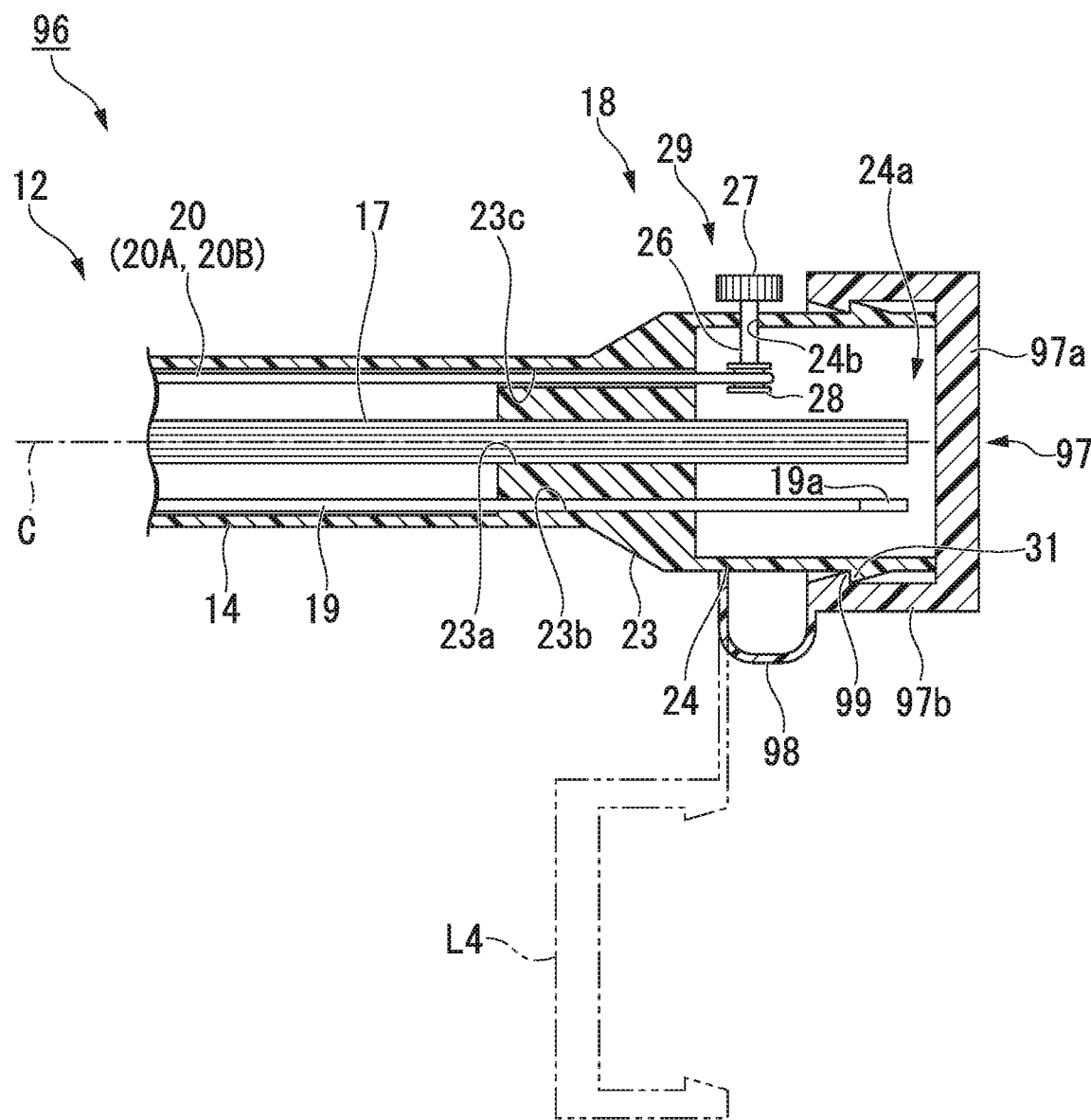
FIG. 10 is a sectional view when a main part of a placement device according to a modification example of the first embodiment of the present invention is viewed in a side view.

According to the present embodiment, as in the placement device 96 shown in FIG. 10, a configuration in which a waterproof cap (sealing member) 97 is connected to the lead cable 12 via an interlocking member 98 may be adopted.

The waterproof cap 97 is formed in a bottomed cylindrical shape. That is, the waterproof cap 97 has a disk-shaped bottom wall portion 97a and a cylindrical peripheral wall portion 97b extending from the outer edge portion toward the distal end side of the bottom wall portion 97a. A second claw 99 is provided on the inner peripheral surface of the distal end portion of the peripheral wall portion 97b. The second claw 99 projects inward in the radial direction of the peripheral wall portion 97b. The second claw 99 engages with the first claw 31 of the first connector 18 from the distal end side of the first claw 31. The bottom wall portion 97a is in contact with the proximal end portion of the first connecting member 24 of the first connector 18. In this way, the waterproof cap 97 covers the opening 24a of the first connector 18 in a watertight manner (hermetically).

The waterproof cap 97 and the interlocking member 98 are integrally formed of an elastic resin material. The interlocking member 98 is elastically deformed and bent. End portions of the interlocking member 98 are respectively connected to the outer peripheral surface of the first connecting member 24 of the first connector 18 and the outer peripheral surface of the peripheral wall portion 97b of the waterproof cap 97.

On the other hand, if the first claw 31 and the second claw 99 disengage from each other in the direction of the axis C by elastically deforming the waterproof cap 97, the waterproof cap 97 is detached from the first connector 18. When the waterproof cap 97 is detached from the first connector 18, the waterproof cap 97 is located at a position shown by a two-dot chain line L4 in FIG. 10, and remains connected to the first connector 18 via the interlocking member 98.

In this way, the waterproof cap 97 is attachable to and detachable from the opening 24a of the first connector 18.

According to the placement device 96 of this modification example, when the proximal end portion of the lead cable 12 is connected to the second connector 38, the waterproof cap 97 is detached from the opening 24a of the lead cable 12. On the other hand, the lead cable 12 can be cleaned in a state where the opening 24a of the lead cable 12 is sealed with the waterproof cap 97 connected to the lead cable 12 via the interlocking member 98. Accordingly, the lead cable 12 can be easily cleaned.

Second Embodiment

Next, a second embodiment according to the present invention will be described with reference to FIG. 11. The same reference numerals will be given to elements that are the same as those according to the above-described embodiment, and description thereof will be omitted. Only different points will be described.

Figure 11:
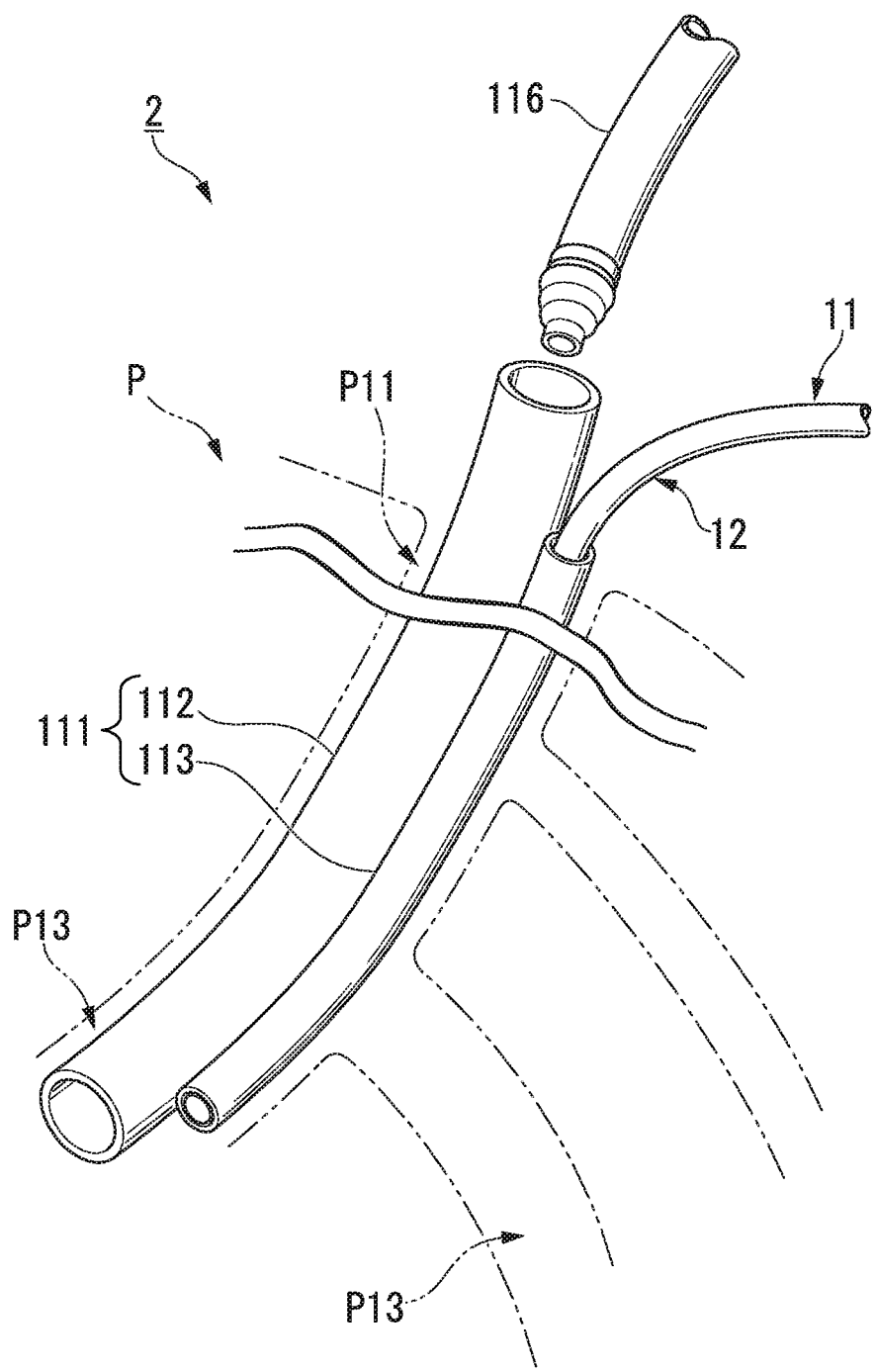
FIG. 11 is a sectional view showing a main part of a placement device according to a second embodiment of the present invention.

As shown in FIG. 11, an placement system 2 according to the present embodiment includes a catheter 111 instead of the catheter 76 of the placement system 1 according to the first embodiment. The catheter 111 has a tube main body 112 and a guide tube 113.

The tube main body 112 is formed in a tubular shape. The outer diameter and the inner diameter of the tube main body 112 are respectively larger than the outer diameter and the inner diameter of the above-described tube main body 77. The outer diameter and the inner diameter of the guide tube 113 are respectively equal to the outer diameter and the inner diameter of the tube main body 77. The length of the tube main body 112 is longer than the length of the guide tube 113. The guide tube 113 is fixed to the outer peripheral surface of the tube main body 112 along the tube main body 112 using an adhesive. The tube main body 112 projects to the distal end side of the guide tube 113. The tube main body 112 projects to the proximal end side of the guide tube 113.

The lead cable 12 of the placement device 11 is inserted into the guide tube 113.

In general, due to poor peristalsis of the larynx (peristalsis, peristaltic movement), children or elderly persons are often dull in the judgment the esophagus or the trachea. Therefore, children or elderly persons may accidentally take food or drinks into their bronchial tubes. The food becomes stuck in the bronchial tubes. In this way, an accident occurs in that breathing is blocked. For example, if a patient who has food stuck in her or his bronchial tubes is neglected for a short period of approximately six minutes, the patient will be in critical condition.

As described above, the placement system 2 according to the present embodiment is used as first aid for a patient who has food stuck in her or his bronchial tubes.

First, as shown in FIG. 11, an aspirator 116 is connected to the proximal end portion of the tube main body 112 of the catheter 111. The lead cable 12 of the placement device 11 is inserted into a guide tube 113 of the catheter 111. While the image observed using the lead cable 12 integrated with the catheter 111 is observed using the display unit 58, the catheter 111 is inserted into a bronchial tube P13 through the nasal cavity or the oral cavity P11 of the patient P. Since the image is observed using the display unit 58, it is possible to check whether or not a foreign substance is stuck in the bronchial tube P13.

After it is checked that the foreign substance is stuck, the aspirator 116 is activated. While a state of the foreign substance projected on the display unit 58 is checked, the foreign substance is aspirated through the tube main body 112 of the catheter 111, or the foreign substance is adsorbed to the tube main body 112. In this manner, treatment is performed so as to pull the foreign substance out of the body of the patient P together with the catheter 111.

For example, in a case where a drug is administered to a lung for a patient suffering from asthma, the drug is usually administered through the larynx. If the placement system 2 according to the present embodiment is used, the catheter 111 and the lead cable 12 are used in order to administer the drug to the lung for the patient whose physical strength is weakened after surgery or an elderly person. While the image is checked using the display unit 58, the catheter 111 can be inserted into the trachea, and the drug can be administered to the lung.

In addition, for example, when an abdominal surgical operation is performed, drainage is performed to discard ascites. After the catheter is installed in a proper place, the catheter may move, and the ascites may be unsuccessfully discarded in some cases. In this case, the lead cable 12 can be inserted into the catheter, and the catheter can be guided such that the catheter is able to being placed in a proper position.

The placement system 2 according to the present embodiment can also be used in cleaning the stomach.

Third Embodiment

Next, a third embodiment according to the present invention will be described with reference to FIG. 12. The same reference numerals will be given to elements that are the same as those according to the above-described embodiments, and description thereof will be omitted. Only different points will be described.

Figure 12:
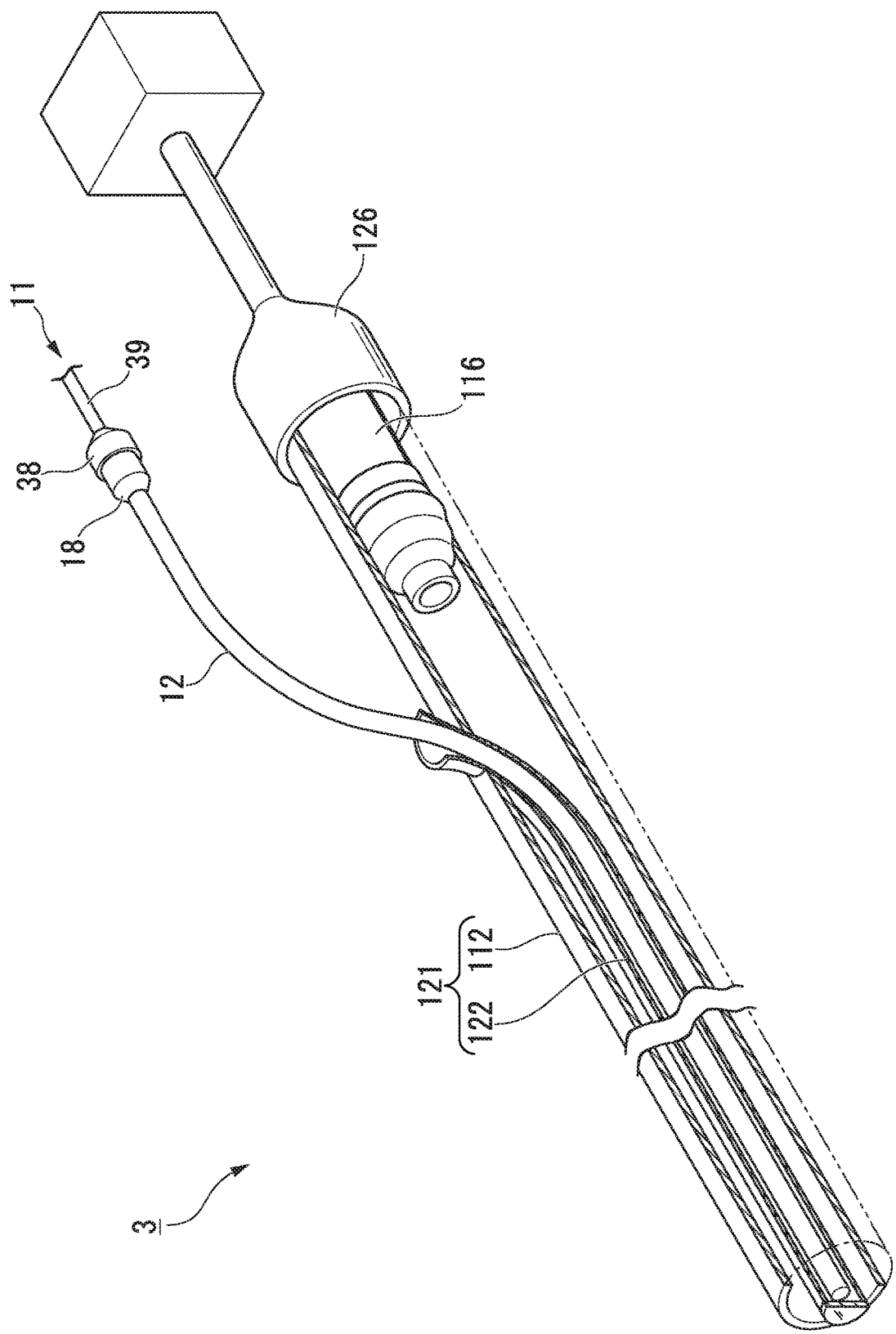
FIG. 12 is a partially broken perspective view showing a placement system according to a third embodiment of the present invention.

As shown in FIG. 12, an placement system 3 according to the present embodiment includes a catheter 121 instead of the catheter 76 of the placement system 1 according to the first embodiment.

The catheter 121 has the tube main body 112 and a guide tube 122.

The guide tube 122 is formed similarly to the guide tube 113. The distal end portion of the guide tube 122 is located coaxially with the tube main body 112 inside the tube main body 112. In the longitudinal direction of the tube main body 112, the distal end portion of the guide tube 122 is located at the same position as the distal end portion of the tube main body 112. The distal end portion of the guide tube 122 is supported by a support member (not shown) relative to the tube main body 112. The support member is located so as not to close a space between the inner peripheral surface of the tube main body 112 and the outer peripheral surface of the guide tube 122. The guide tube 122 extends to the proximal end side along the tube main body 112.

The proximal end portion of the guide tube 122 penetrates the tube main body 112 in the radial direction, in an intermediate portion of the tube main body 112 in the longitudinal direction. The proximal end portion of the guide tube 122 projects outward in the radial direction from the outer peripheral surface of the tube main body 112.

Similar to the placement system 2 according to the second embodiment, the placement system 3 according to the present embodiment configured in this way is used as first aid for a patient who has food stuck in her or his bronchial tubes.

First, the aspirator 116 is connected to the proximal end portion of the tube main body 112 of the catheter 121. It is preferable that a connecting portion between the tube main body 112 and the aspirator 116 be covered with a cap 126 in an airtight manner (hermetically). The lead cable 12 of the placement device 11 is inserted into the guide tube 122 of the catheter 121. In this case, it is preferable that the distal end portion of the lead cable 12 be located slightly close to the proximal end side from the distal end portion of the guide tube 122.

The subsequent steps are similar to those of the placement system 2 according to the second embodiment. The catheter 121 is used after being inserted into the bronchial tube P13 of the patient P.

Fourth Embodiment

Next, a fourth embodiment according to the present invention will be described with reference to FIGS. 13 and 14. The same reference numerals will be given to elements that are the same as those according to the above-described embodiments, and description thereof will be omitted. Only different points will be described.

Figure 13:
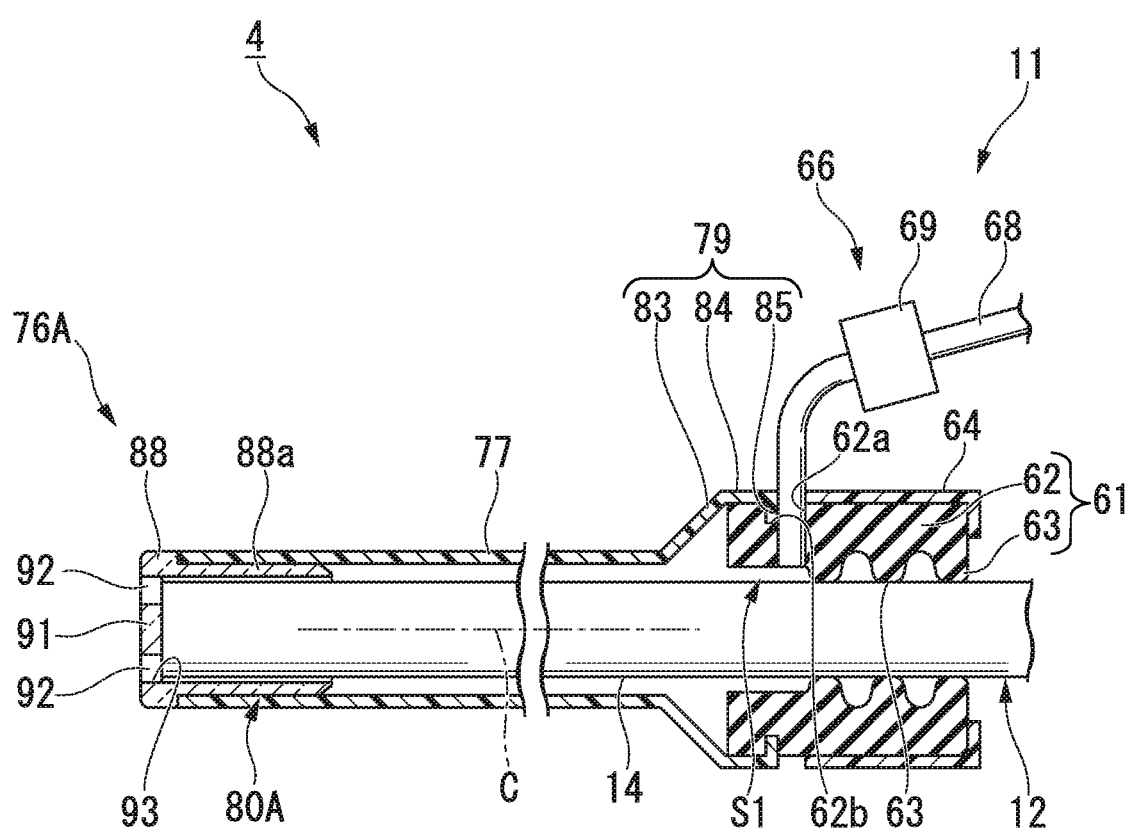
FIG. 13 is a partially broken side view showing a system according to a fourth embodiment of the present invention.
Figure 14:
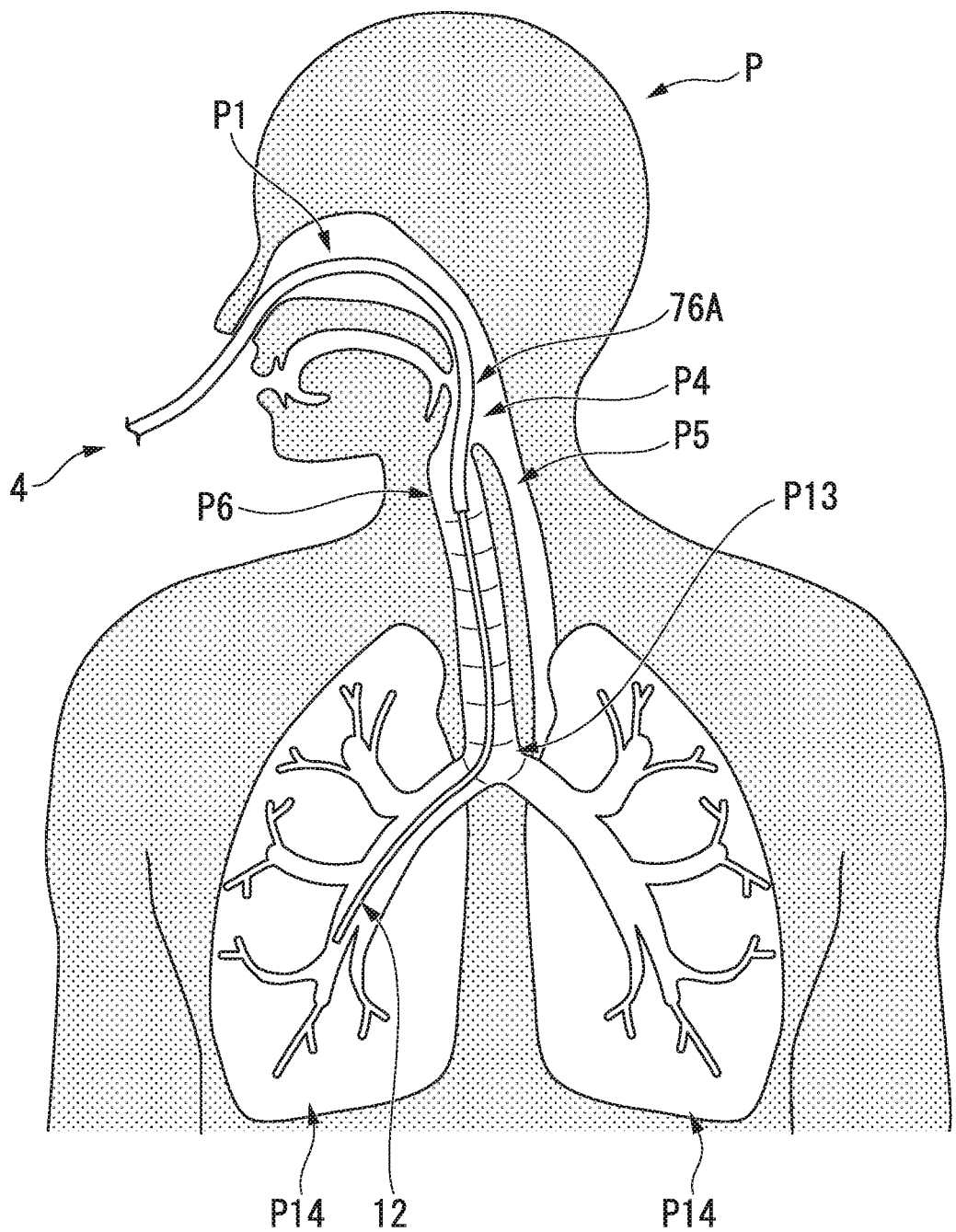
FIG. 14 is a view for describing a method of using the system.

As shown in FIG. 13, a system 4 according to the present embodiment includes a catheter 76A instead of the catheter 76 of the placement system 1 according to the first embodiment. The catheter 76A is different from the catheter 76 in that the catheter 76A has a distal end side locking member 80A.

The distal end side the locking member 80A includes the cylindrical body 88, a transparent member 91, and a bridge portion 92.

The transparent member 91 is located inside an opening portion on the distal end side of the cylindrical body 88. The transparent member 91 is formed in a circular shape coaxially with the cylindrical body 88. The outer diameter of the transparent member 91 is smaller than the inner diameter of the cylindrical body 88. An annular gap 93 is provided between the inner peripheral surface of the cylindrical body 88 and the outer peripheral surface of the transparent member 91. The transparent member 91 is transparent to such an extent that an observation target located on the distal end side of the transparent member 91 is observable using the lead cable 12 locked to the transparent member 91 from the proximal end side.

The bridge portion 92 interlocks the cylindrical body 88 and the transparent member 91 with each other. A plurality of bridge portions 92 are intermittently provided in the gap 93 in the circumferential direction. The bridge portion 92 is rigid to such an extent that the bridge portion 92 can be broken, for example, when the transparent member 91 is pressed from the proximal end side by the lead cable 12.

Next, a method of utilizing the system 4 configured as described above will be described. As shown in FIG. 14, the system 4 utilizes the catheter 76A so as to guide the lead cable 12 into the body while the lead cable 12 is prevented from being contaminated. In the present embodiment, a case where the system 4 is used so as to guide the lead cable 12 into a lung P14 will be described as an example.

First, a user utilizes the supply member 61 as described above so as to insert the lead cable 12 into the catheter 76A. In this case, the distal end surface of the lead cable 12 is locked to the transparent member 91 of the catheter 76A.

While the image obtained by the observation of the lead cable 12 is checked using the display unit 58 via the transmission unit 36, the catheter 76A is inserted through the nasal cavity P1 (opening of the body) of the patient P. In this case, if the gas is supplied from the supply member 61, as described above, the gas flows between the inner surface of the catheter 76A and the outer peripheral surface of the lead cable 12, and the gas is discharged outward from the catheter 76A through the gap 93. In this manner, it is possible to prevent the body fluid of the patient P from adhering to and contaminating the catheter 76A and the lead cable 12.

When the distal end of the catheter 76A is located in the pharynx P4, the lead cable 12 is operated so as to press the lead cable 12 against the transparent member 91. In this case, the bridge portion 92 is broken, and the lead cable 12 is exposed outward through the catheter 76A for the first time. After being inserted into the trachea P6, the exposed lead cable 12 is guided into the lung P14 through the bronchial tube P13. As described above, the lead cable 12 is covered with the catheter 76A up to the pharynx P4, and is not substantially contaminated. Therefore, very accurate observation can be realized by using the lead cable 12 so as to observe the inside of the lung P14.

In the present embodiment, the transparent member 91 is interlocked with the cylindrical body 88 via the bridge portion 92. However, the present invention is not limited thereto. For example, the transparent member 91 may be formed into a film which easily breakable, and may seal the distal end of the cylindrical body 88.

Furthermore, the distal end side of the locking member 80A may not be provided. Even in this case, when the catheter 76A is inserted into the body, the gas is continuously supplied from the supply member 61. In this manner, for example, the body fluid can be prevented from adhering to the lead cable 12 inside the catheter 76A.

Fifth Embodiment

Next, a fifth embodiment according to the present invention will be described with reference to FIG. 15. The same reference numerals will be given to elements that are the same as those according to the above-described embodiments, and description thereof will be omitted. Only different points will be described.

Figure 15:
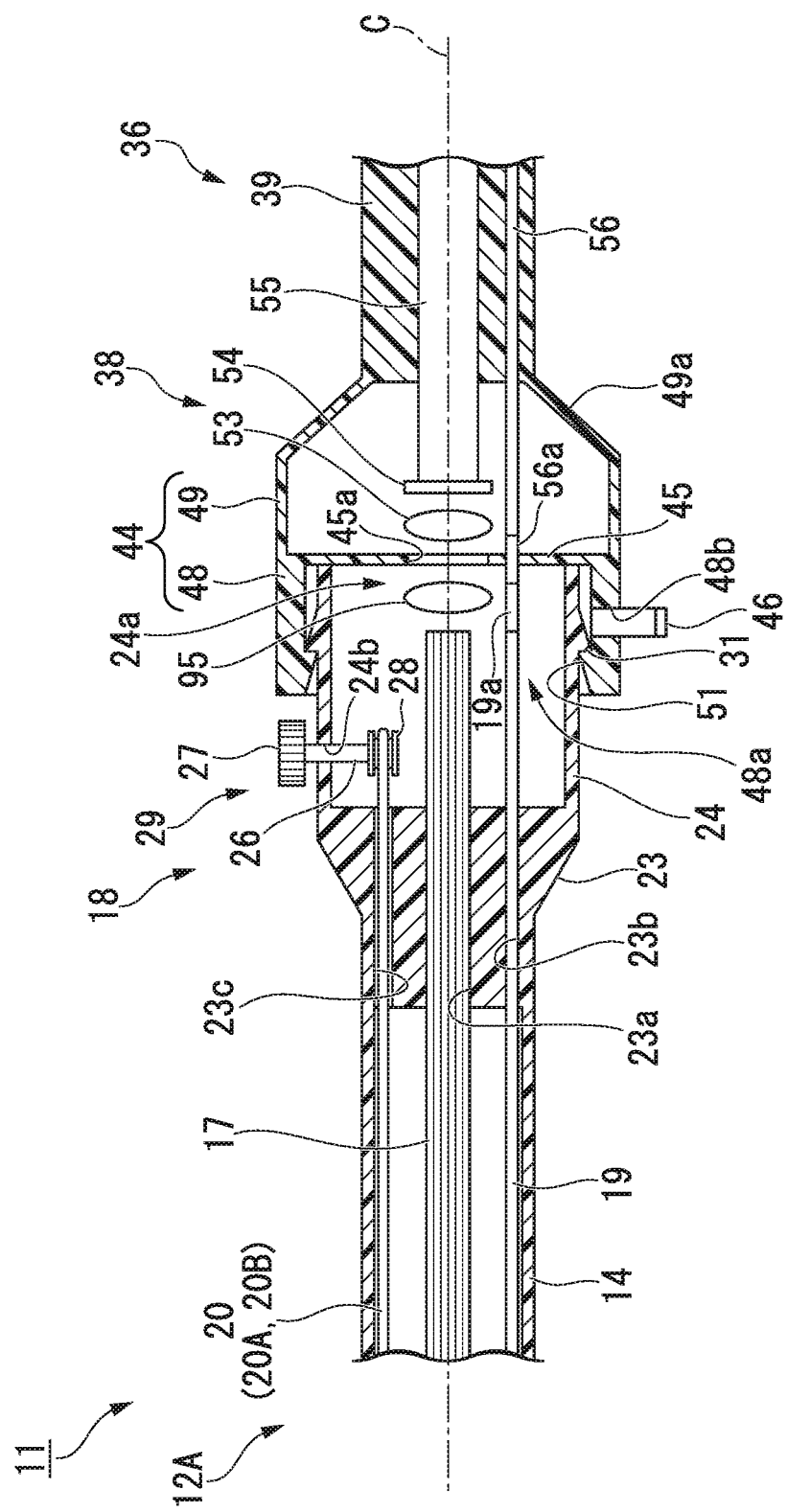
FIG. 15 is a sectional view when a state where a first connector of a lead cable and a second connector of a display unit are connected to each other is viewed in a side view according to a fifth embodiment of the present invention.

As shown in FIG. 15, in a lead cable 12A according to the present embodiment, a lens 95 or a transparent cover is located inside the first connecting member 24 (inside the opening 24a). The lens 95 or the transparent cover is located on the proximal end side of the lead cable 12A from the optical fiber 17. The lens 95 or the transparent cover is located coaxially (on the axis C) with the optical fiber 17. In other words, the proximal end portion of the optical fiber 17 is covered by the lens 95 or the transparent cover from the proximal end side (in the direction of the axis C).

According to the present embodiment, the light guided to the proximal end side through the inside of the optical fiber 17 is incident on the lens 95 and the lens 53. In this manner, for example, it is possible to reduce the possibility of an image being formed as a virtual image on the light receiving surface of the imaging element 54. Alternatively, it is possible to reduce image distortion by combining a concave lens and a convex lens with each other.

According to the present embodiment, the optical fiber 17 is protected by the lens 95 or the transparent cover. Therefore, the lens 95 or the transparent cover prevents dust or dirt from adhering to the optical fiber 17.

The first to fifth embodiments according to the present invention have been described above in detail with reference to the drawings. Specific configurations are not limited to these embodiments. The present invention also includes modifications, combinations, or deletions of the configurations within the scope not departing from the gist of the present invention. Furthermore, as a matter of course, the configurations described in the respective embodiments can be utilized in appropriate combination with each other.

For example, according to the first to fourth embodiments, the imaging element 54 is located inside the transmission unit 36. However, the imaging element 54 may be located inside the lead cable 12. In this case, for example, the imaging element 54 is located on the proximal end side of the condenser lens 16 so as to be adjacent to the condenser lens 16, and a signal line is connected to the imaging element 54. The image acquired by the imaging element 54 is converted into a signal by the imaging element 54, and the transmission unit transmits the signal converted from the image.

The placement device 11 may not include the imaging element 54, and the image obtained by the observation of the lead cable 12 may be transmitted to the proximal end side by the optical fiber. In this case, the image obtained by the observation of the lead cable 12 is displayed on the display unit without being converted into the signal.

The placement device 11 may not include the display unit 58 and the supply member 61. In a case where the placement device 11 does not include the display unit 58, a computer display may be used as the display unit. The placement device and a computer may be connected to each other by using a wire such as a Universal Serial Bus (USB) cable. In addition, a display of a portable terminal such as a smartphone may be used as the display unit. The placement device and the portable terminal may be wirelessly connected to each other. Communication standards such as Wi-Fi (registered trademark) and wireless local area network (LAN) can be used for the wireless connection.

The LED 15 may not be in contact with the condenser lens 16. The placement device 11 may not include the operation wire 20 and the bending controller 29.

In the placement system 1, the proximal end side projection 90 may not be locked to the distal end surface of the lead cable 12. The whole linear member 78 may be buried into the tube main body 77.

In the present specification, the invention described below is also disclosed.

APPENDIX CLAIM 1

A placing method of a catheter, comprising:
inserting an insertion unit into the catheter, the insertion unit being flexible and being capable of observing an object located more distally than a distal end of the insertion unit;
inserting the catheter having the inserted insertion unit through an opening of a human body, while observing an image obtained by observation of the insertion unit via a transmission unit having a first connecting portion connected to a proximal end portion of the insertion unit;
causing the catheter to place the inside of the body after drawing the insertion unit out from the catheter;
detaching the insertion unit from the first connecting portion; and
attaching a new insertion unit to the first connecting portion.

Those skilled in the art will recognize, or be able to ascertain using no more than routine experimentation, many equivalents of the specific embodiments disclosed herein. Such equivalents are intended to be encompassed by the following claims.

The invention claimed is:
1. A placement device for causing a catheter to place an inside of a body, the device comprising:
an insertion unit which is flexible, and which is capable of being inserted into and removed from the catheter, the insertion unit being capable of observing an object located more distally than a distal end of the insertion unit;
a transmission unit which has a first connecting portion to be detachably connected to a proximal end portion of the insertion unit, and which transmits an image obtained by observation of the insertion unit or a signal obtained by converting the image; and
a supply member into which the insertion unit is to be inserted so as to be drawable therefrom, and to which a proximal end portion of the catheter is to be detachably attached,
wherein the supply member includes:
a supply unit main body formed in a cylindrical shape into which the insertion unit is to be inserted, and
a projection, formed of an elastic material, the projection on an inner peripheral surface of the supply unit main body, and which contacts with the insertion unit hermetically and holds the insertion unit such that the insertion unit is capable of sliding, the projection surrounding the insertion unit from a proximal end to a distal end of the supply unit main body, and wherein:
a through-hole is formed at a position closer to the distal end of the supply unit main body than the proximal end of the supply unit main body;
the through-hole is formed on the inner peripheral surface of the supply unit main body; and
the through-hole communicates:
with an inside of the supply unit main body, and
at the distal end of the supply unit main body.

2. The placement device according to claim 1, wherein a plurality of projections are arranged on the inner peripheral surface of the supply unit main body.

3. The placement device according to claim 1, wherein the supply unit main body and the projection are integrally formed of an elastic material.

4. The placement device according to claim 1, wherein:
a locking portion is provided at the proximal end portion of the catheter, and
a locked portion is formed over an entire periphery of the supply unit main body on an outer peripheral surface of the supply unit main body and the locking portion is locked to the locked portion.

5. The placement device according to claim 1, wherein the insertion unit has:
a condenser lens which collects light from the distal end of the insertion unit, and
a light source which emits the light to the distal end of the insertion unit, which generates heat, and which comes into contact with the condenser lens.

6. The placement device according to claim 1, wherein an imaging element for acquiring the image is located inside the transmission unit.

7. The placement device according to claim 1, wherein:
a second connecting portion having a second opening is provided in the proximal end portion of the insertion unit, and
a sealing member which is detachable from the second opening and which hermetically covers the second opening is connected to the insertion unit via an interlocking member.

8. The placement device according to claim 1, wherein the insertion unit includes an outer cover tube, an optical fiber inserted into the outer cover tube, and a lens or a transparent cover which covers the optical fiber from a proximal end side.

9. A placement system comprising:
the placement device according to claim 1; and
the catheter.

10. The placement system according to claim 9, wherein the catheter includes:
a tube main body that is formed in a tubular shape, and into which the insertion unit is inserted, and
a first projection which projects inward in a radial direction from an inner peripheral surface of a distal end portion of the tube main body, and which is locked with a distal end surface of the insertion unit.

11. The placement system according to claim 10, wherein the first projection is provided in only a portion of the tube main body in a circumferential direction of the tube main body.

12. The placement system according to claim 10, wherein the catheter includes a second projection which projects inward in the radial direction from an inner peripheral surface of the tube main body.

13. The placement system according to claim 10, wherein the catheter includes a linear member which is formed of a more rigid material than the tube main body, and which is provided in the tube main body along an axis of the tube main body.

14. The placement system according to claim 13, wherein:
a portion of the linear member projects inward in the radial direction from an inner peripheral surface of the tube main body, and
a remaining portion of the linear member is buried into the tube main body.

15. The placement system according to claim 9, further comprising a fluid supply unit which supplies a fluid to the through-hole.

16. A placement system comprising:
the placement device according to claim 1;
the catheter,
wherein the catheter has a tube main body which is formed in a tubular shape; and
a guide tube into which the insertion unit is inserted, the guide tube being attached to an outer peripheral surface of the tube main body or being located inside the tube main body.

17. The placement system according to claim 15, wherein the fluid supply unit includes a pressure feeding tube whose distal end portion is to be inserted into the through-hole.

* * * * *